United States Patent
Nakamura et al.

(10) Patent No.: US 6,316,485 B1
(45) Date of Patent: Nov. 13, 2001

(54) 1,5-DIPHENYLPYRAZOLE DERIVATIVES

(75) Inventors: Katsuya Nakamura, Takatsuki; Kazuo Okumura, Osaka; Takashi Ogino, Yamatokoriyama; Takeshi Kato, Nishinomiya; Hirofumi Yamamoto, Takarazuka; Tadashi Terasaka, Ikeda; Yuka Noda, Takarazuka, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/508,507

(22) PCT Filed: Sep. 14, 1998

(86) PCT No.: PCT/JP98/04150

§ 371 Date: Mar. 23, 2000

§ 102(e) Date: Mar. 23, 2000

(87) PCT Pub. No.: WO99/15505

PCT Pub. Date: Apr. 1, 1999

(30) Foreign Application Priority Data

Sep. 24, 1997 (AU) .................................................. PO9414

(51) Int. Cl.[7] .......................... A61K 31/415; A61P 29/00; C07D 231/16
(52) U.S. Cl. .................... 514/406; 548/375.1; 548/377.1
(58) Field of Search ............................. 548/375.1, 377.1; 514/406

(56) References Cited

U.S. PATENT DOCUMENTS 5,134,142   7/1992   Matsuo et al. .
5,550,147   8/1996   Matsuo et al. .
5,670,533   9/1997   Matsuo et al. .

FOREIGN PATENT DOCUMENTS

WO 97/13755   4/1997   (WO) .

*Primary Examiner*—Robert W. Ramsuer
(74) *Attorney, Agent, or Firm*—Oblon, Spivak, McClelland, Maier & Neustadt, P.C.

(57) ABSTRACT

A compound of the formula (I):

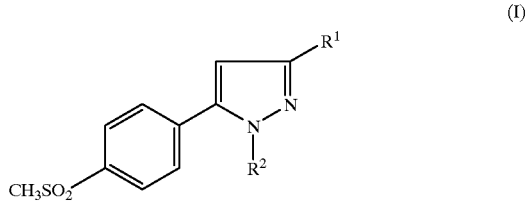

wherein:
$R^1$ is chlorine, difluoromethyl, trifluoromethyl or cyano; and
$R^2$ is a group having the formula:

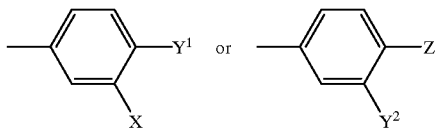

wherein:
X is halogen, cyano, nitro or amino;
$Y^1$ is lower alkyl or lower alkoxy; and
Z is halogen;
or a pharmaceutically acceptable salt thereof.

14 Claims, No Drawings

1,5-DIPHENYLPYRAZOLE DERIVATIVES

This application is a 371 of PCT/JP98/04150 filed Sep. 14, 1998.

TECHNICAL FIELD

This invention relates to novel pyrazole compounds and the salts thereof having pharmacological activity; to a process for their production; and to a pharmaceutical composition containing the same.

BACKGROUND OF ART

Some pyrazole derivatives having antiinflammatory and analgesic activities have been known as described, for example, in Canadian Patent 1 130 808, and EP Patent Publication Nos. 248 594, 272 704, 293 220, 418 845 and 554 829, and WO Patent Publication Nos. 95/15315, 95/15316, 95/15317, 95/15318, 96/14302 and 97/15271.

DISCLOSURE OF THE INVENTION

One object of this invention is to provide the novel pyrazole compounds and salts thereof which have an inhibiting activity of cyclooxygenase-2.

Another object of this invention is to provide the process for production of the novel pyrazole compounds.

A further object of this invention is to provide the pharmaceutical composition containing, as an active ingredient, the pyrazole compound or a salt thereof.

A still further object of this invention is to provide a use of the novel pyrazole compounds and salts thereof for manufacturing a medicament for treating or preventing various diseases.

The present invention relates to the novel pyrazole compounds and the salts thereof, which have pharmaceutical activity such as inhibiting activity of cyclooxygenase-2 (hereinafter described as COX-II), to a process for their production, to a pharmaceutical composition containing the same, and to a use thereof.

The object pyrazole derivatives of this invention are new and can be represented by the following general formula (I).

(I)

wherein
$R^1$ is chlorine, difluoromethyl, trifluoromethyl or cyano, and
$R^2$ is a group having the following formula

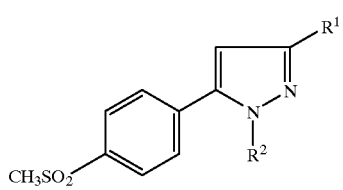

-continued

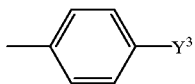

wherein
X is halogen, cyano, nitro or amino,
$Y^1$ is lower alkyl or lower alkoxy,
$Y^2$ is lower alkyl or lower alkoxy,
$Y^3$ is ethyl, n-propyl or isopropyl, and
Z is hydrogen or halogen, and a salt thereof.

The object compound (I) can be prepared by one of the following processes 1–4.

Process 1

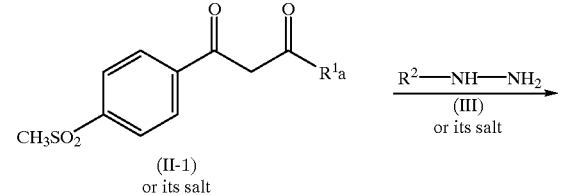

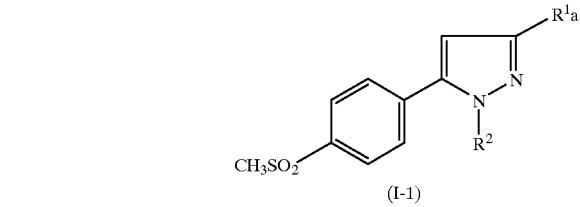

Process 2

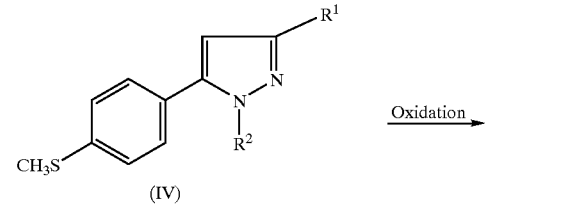

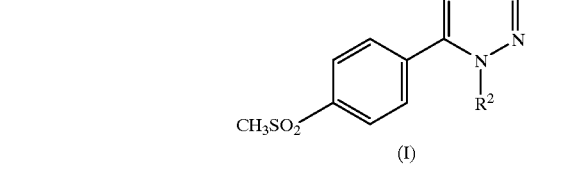

Process 3

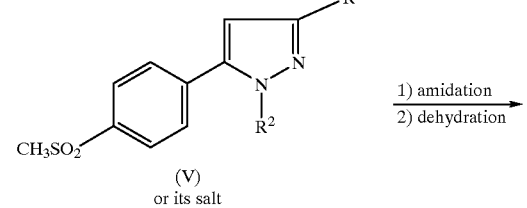

Process 4

(VI) or its salt —Chlorination→ (I-3)

Reference Processes (1) (II-2) or its salt + R²—NH—NH₂ (III) or its salt → (IV-1)

(2) (II-3) or its salt + R²—NH—NH₂ (III) or its salt → (V) or its salt (3) (VII) + R²—NH—NH₂ (III) or its salt → (VI) or its salt wherein $R^1$ and $R^2$ are each as defined above, $R^1a$ is difluoromethyl or trifluoromethyl, and $R^3$ is carboxy or esterified carboxy.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" and lower alkyl moiety in the terms "lower alkoxy" may be a straight or branched one such as methyl, ethyl, n-propyl, isopropyl, butyl, isobutyl, tert-butyl, pentyl, hexyl, and the like, in which preferable one is methyl.

Suitable "lower alkoxy" may be methoxy, ethoxy, and the like, in which preferable one is methoxy.

Suitable "halogen" may be fluorine, chlorine, bromine and iodine.

Suitable "esterified carboxy" may be lower alkoxycarbonyl, such as methoxycarbonyl, ethoxycarbonyl, tert-butoxycarbonyl, and the like, in which preferable one is ethoxycarbonyl.

In the compounds (I), the preferred ones are recited. Compounds having the formula (I)

wherein $R^1$ is chlorine, difluoromethyl, trifluoromethyl or cyano, and $R^2$ is a group having the formula wherein X is halogen, cyano or nitro, $Y^1$ is lower alkyl or lower alkoxy, $Y^2$ is lower alkyl or lower alkoxy, and Z is hydrogen or halogen.

Compounds having the formula (I)

wherein $R^1$ is chlorine, and $R^2$ is a group having the formula

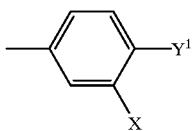

wherein X is halogen or cyano, and $Y^1$ is lower alkoxy.

Compounds having the formula (I)
wherein
$R^1$ is trifluoromethyl, and
$R^2$ is a group having the formula

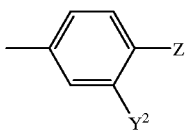

wherein $Y^2$ is lower alkyl, and Z is hydrogen.

Compounds having the formula (I)
wherein
$R^1$ is chlorine or trifluoromethyl, and
$R^2$ is a group having the formula

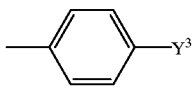

wherein $Y^3$ is ethyl, n-propyl or isopropyl.

The more preferred one is the compound selected from the group consisting of (1) 1-(3-methylphenyl)-5-[4-(methylsulfonyl)phenyl]-3-(trifluoromethyl)pyrazole,
(2) 3-chloro-1-(3-cyano-4-methoxyphenyl)-5-[4-(methylsulfonyl)phenyl]pyrazole,
(3) 3-chloro-1-(3-chloro-4-methoxyphenyl)-5-[4-(methylsulfonyl)phenyl]pyrazole,
(4) 3-chloro-1-(3-chloro-4-methylphenyl)-5-[4-(methylsulfonyl)phenyl]pyrazole,
(5) 3-chloro-1-(3-fluoro-4-methylphenyl)-5-[4-(methylsulfonyl)phenyl]pyrazole,
(6) 1-(3-fluoro-4-methoxyphenyl)-5-[4-(methylsulfonyl)phenyl]-3-(trifluoromethyl)pyrazole,
(7) 3-(difluoromethyl)-1-(3-fluoro-4-methoxyphenyl)-5-[4-(methylsulfonyl)phenyl]pyrazole,
(8) 3-chloro-1-(4-chloro-3-methylphenyl)-5-[4-(methylsulfonyl)phenyl]pyrazole,
(9) 1-(4-chloro-3-methoxyphenyl)-5-[4-(methylsulfonyl)phenyl]pyrazole-3-carbonitrile,
(10) 3-chloro-1-(4-isopropylphenyl)-5-[4-(methylsulfonyl)phenyl]pyrazole and
(11) 3-chloro-1-(3-chloro-4-ethylphenyl)-5-[4-(methylsulfonyl)pheny]pyrazole.

The compounds (I) according to the present invention may contain one or more asymmetric centers, and thus they can exist as enantiomers or diastereoisomers, and the invention includes both mixtures and separate individual isomers.

Suitable salts of the compounds (I) are conventional pharmaceutically acceptable salts and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, magnesium salt etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like, and the preferable example thereof is an acid addition salt.

The compound (I) according to the present invention can be in the form of a solvate, which was included within the scope of the present invention. The solvate preferably includes a hydrate, an ethanolate, and so on.

Also included in the scope of invention are radiolabelled derivatives of compounds (I) which are suitable for biological studies.

Process 1

The compound (I-1) can be prepared by reacting the compound (II-1) or its salt with a hydrazine derivative (III) or its salt.

The reaction is usually carried out in a conventional solvent such as water, alcohol [e.g., methanol, ethanol, isopropyl alcohol, etc.], alkanoic acid, tetrahydrofuran, dioxane, toluene, methylene chloride, chloroform, N,N-dimethylformamide, or any other organic solvents which do not adversely affect the reaction, or the mixture thereof, preferably, acidic solvent such as alkanoic acid (e.g., acetic acid).

The reaction temperature is not critical and the reaction is usually carried out under cooling to warming.

Process 2

The compound (I) can be prepared by reacting a compound (IV) with an oxidizing agent.

The suitable oxidizing agent may be hydrogen peroxide, cumene hydroperoxide, tert-butyl hydroperoxide, Jones reagent, peracid [e.g. peracetic acid, perbenzoic acid, m-chloroperbenzoic acid, monopersulfate compound (Oxone®), etc.], chromic acid, potassium permanganate, alkali metal periodate [e.g. sodium periodate, etc.], and the like.

This reaction is usually carried out in a solvent which does not adversely influence the reaction such as acetic acid, dichloromethane, acetone, ethyl acetate, chloroform, water, an alcohol [e.g. methanol, ethanol, etc.], a mixture thereof or the like.

The reaction temperature is not critical, and the reaction is usually carried out under cooling to warming.

Process 3

The compound (I-2) can be prepared from the compound (V) or its salt by the following methods. Namely, (i) the compound (V) or its salt can be subjected to an amidation to give a corresponding carbamoyl derivatives, and then (ii) the corresponding carbamoyl derivatives can be subjected to a dehydration to give the compound (I-2).

Amidation is carried out in a conventional manner, which is capable of converting carboxy group or protected carboxy group to carbamoyl group. Amidation can preferably carried out by, for example, (i) reacting the compound (V), wherein $R^2$ is esterified carboxy, with alkanoylamine (e.g., acetamide, formamide, etc.) in the presence of organic base (e.g., sodium alkoxide, etc.) or (ii) reacting the compound (V), wherein $R^2$ is carboxy, or its salt, with ammonia or its salt in the presence of condensing agent.

Dehydration is carried out in the conventional manner, which is capable of dehydrating a carbamoyl group to cyano group, and suitable dehydrating agent may be phosphorus compound (e.g., phosphorus oxychloride, etc.) or the like.

The reaction is usually carried out in a conventional solvent such as alcohol [e.g., methanol, ethanol, isopropyl alcohol, etc.], tetrahydrofuran, dioxane, toluene, methylene chloride, chloroform, N,N-dimethylformamide, or any other organic solvents which do not adversely affect the reaction, or the mixture thereof.

The reaction temperature is not critical and the reaction is usually carried out; under cooling to warming.

Process 4

The compound (I-3) can be prepared by the following methods.

Namely, 1) the compound (VI) or its salt is firstly reacted with a nitrite compound, and then 2) the resulting product is reacted with cuprous chloride.

Suitable nitrite compound may be alkali metal nitrite [e.g. sodium nitrite, potassium nitrite, etc.], alkyl nitrite [e.g. isoamyl nitrate, tert-butyl nitrite, etc.], and the like.

In the first step, the reaction is preferably carried out in the presence of an acid [e.g. hydrochloric acid, sulfuric acid, etc.].

The reaction is usually carried out in a solvent such as water, tetrahydrofuran, dioxane, acetonitrile, or any other organic solvent which does not adversely influence the reaction, or a mixture thereof.

The reaction temperature is not critical and the reaction can be carried out under cooling to warming.

In the second step, the reaction is preferably carried out in the presence of alkali metal halide [e.g. sodium chloride, etc.] and an inorganic acid [e.g. hydrochloric acid, etc.].

The reaction is usually carried out in a solvent such as water, tetrahydrofuran, dioxane, or any other organic solvent which does not adversely influence the reaction, or a mixture thereof.

The reaction temperature is not critical and the reaction can be carried out warming to heating.

Reference Processes

The compound (IV), (V) and (VI) are prepared by reacting the compound (III) with the compounds (II-2), (II-3) and (VII) respectively in a similar manner to those of Process 1 and below mentioned Preparations.

The compounds obtained by the above processes can be isolated and purified by a conventional method such as pulverization, recrystallization, column chromatography, reprecipitation, or the like.

Suitable salts of the compounds (III) and (VI) include an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, sulfate, phosphate, etc.], and the like.

Suitable salts of the compound (II-1), (II-2), (II-3) and (V) are an alkali metal salt [e.g. sodium salt, potassium salt, etc.], an alkaline earth metal salt [e.g. calcium salt, magnesium salt, etc.], and the like.

The object compound (I) possesses inhibiting activity of COX-II and possesses strong antiinflammatory, analgesic, antithrombotic, anti-cancer activities and so on. The object compound (I) and pharmaceutically acceptable salts thereof, therefore, are useful for the treatment and/or prevention of inflammatory conditions, various pains, collagen diseases, autoimmune diseases, various immunological diseases, thrombosis, cancer and neurodegenerative diseases in human beings or animals, and more particularly for the treatment and/or prevention of inflammation and pain in joint and muscle [e.g. rheumatoid arthritis, rheumatoid spondylitis, osteoarthritis, gouty arthritis, juvenile arthritis, etc.], inflammatory skin condition [e.g. sunburn, burns, eczema, dermatitis, etc.], inflammatory eye condition [e.g. conjunctivitis, etc.], lung disorder in which inflammation is involved [e.g. asthma, bronchitis, pigeon fancier's disease, farmer's lung, etc.], condition of the gastrointestinal tract associated with inflammation [e.g. aphthous ulcer, Chrohn's disease, atopic gastritis, gastritis varialoforme, ulcerative colitis, coeliac disease, regional ileitis, irritable bowel syndrome, etc.], gingivitis, inflammation, pain and tumescence after operation or injury, pyrexia, pain and other conditions associated with inflammation, particularly those in which lipoxygenase and cyclooxygenase products are a factor, systemic lupus erythematosus, scieroderma, polymyositis, tendinitis, bursitis, periarteritis nodosa, rheumatic fever, Sjogren's syndrome, Behcet disease, thyroiditis, type I diabetes, nephrotic syndrome, aplastic anemia, myasthenia gravis, uveitis contact dermatitis, psoriasis, Kawasaki disease, sarcoidosis, Hodgkin's disease, Alzheimer's disease, and the like. Additionally, the object compound (I) or a salt thereof is expected to be useful as therapeutical and/or preventive agents for cardiovascular or cerebrovascular diseases, the diseases caused by hyperglycemia and hyperlipemia.

The compound (I) of the present invention has much advantage, such as more selective inhibitory activity of COX-II, stronger activity, more suitable half-life, decreased adverse effect, or the like, compared to the known pyrazole compounds shown in the prior arts.

In order to illustrate the usefulness of the object compound (I), the pharmacological test data of the compound (I) are shown in the following.

[A] Antiinflammatory Activity

Effect on Adjuvant Arthritis in Rats (i) Test Method:

Ten female Sprague-Dawley rats were used per group. A dose of 0.5 mg of Mycobacterium tuberculosis (strain M37 BA) suspended in 0.05 ml of liquid paraffin was injected subcutaneously in the right hind paw. The injection of mycobacterial adjuvant produced local inflammatory lesions (primary lesion) and then about 10 days later, secondary lesions in both the injected and uninjected paws. The volumes of both paws before and on days 23 after the injection was measured as percent inhibition in comparison to vehicle-treated controls. The drug was given orally once a day for 23 consecutive days from day 1 after the injection.

(ii) Test Results:

[A] Antiinflammatory Activity

| Test compound (Example No.) | Dose (mg/kg) | Inhibition of secondary lesion (uninjected paw) (%) |
|---|---|---|
| 1 | 1.0 | ≧60 |
| 10-(8) | 1.0 | ≧60 |

[B] COX-I and COX-II Activity in vitro (i) Test Method:

a. Preparation of the recombinant cyclooxygenase (COX)

The human cyclooxygenase COX-I and COX-II were expressed in transfected Chinese hamster ovary (CHO) cells. Monolayer cultures of semi-confluent CHO cells stably expressing COX-I and COX-II were washed twice and scraped into phosphate buffered saline (PBS). The cells were centrifuged at 200×g for 5 minutes and the cell pellet was sonicated in reaction buffer containing 100 mM Tris-HCl (pH 7.4), 2 μM hematin and 5 mM tryptophan. Broken cells were centrifuged for 5 minutes at 1700×g at 4° C. and the supernatants were used as crude enzymes.

Cyclooxygenase activities in the absence or presence of inhibitors were measured by determining the level of prostaglandin $E_2$ ($PGE_2$) synthesis from arachidonic acid. Enzymes (1 μg for COX-I and/or 3 μg for COX-II) in a total volume of 200 μl of reaction buffer were incubated in the absence and presence of various concentrations of inhibitors for 5 minutes at 30° C. The reaction was then started by the addition of arachidonic acid to the final concentration of 10 μM. The reaction was terminated by 50 μl of HCl (1N) after incubation at 30° C. for 5 minutes. $PGE_2$ was extracted with ethyl acetate, concentrated under a stream of nitrogen and analyzed by a radio immunoassay kit (Amersham) according to the manufacture's instructions.

b. Assay for human recombinant COX-I and COX-II activity

COX activity was assayed as $PGE_2$ formation using radioimmunoassay to detect the prostaglandin release. The appropriate COX enzyme was incubated in 0.1 M Tris-HCl buffer (pH 7.3) containing hematin and tryptophan with the addition of arachidonic acid (10 μM) for 5 minutes at 37° C. Compounds were pre-incubated with the enzyme for 5 minutes prior to the addition of arachidonic acid. Any reaction between the arachidonic acid and the enzyme was stopped after 5 minutes at 37° C. by addition of 20 μl of 1N HCl. $PGE_2$ formation was measured by radioimmunoassay (Amersham).

(ii) Test Results:

[B] COX-I and COX-II Activity in vitro

| Test compound (Example No.) | Human COX-II $IC_{50}$ (μM) | Human COX-I $IC_{50}$ (μM) |
|---|---|---|
| 3-(16) | <1 | >100 |
| 6 | <1 | >100 |
| 10-(8) | <1 | >100 |

The compound (I) and a pharmaceutically acceptable salt thereof, are used as a medicament by intravenous, intracutaneous, intramuscular, pulmonary, or oral administration, or insufflation to human beings or animals.

A pharmaceutical composition of the present invention is a homogeneous mixture which comprises one of the compounds (I) or pharmaceutically acceptable salts thereof, as an active ingredient, in association with a pharmaceutically acceptable carrier or excipient. The pharmaceutical composition is manufactured by mixing the sufficient amount of the compound (I) or a salt thereof as an active ingredient with a pharmaceutically non-toxic carrier or excipient to give homogeneous mixture. The pharmaceutically non-toxic carriers and excipients may be organic or inorganic and solid or liquid, and can be any of the conventional ones suitable for oral, parenteral or external (topical) administration.

For therapeutic purpose, the pharmaceutical composition of the present invention can be used in a form of a pharmaceutical preparation, for example, in a solid, semisolid, or liquid form. The pharmaceutical preparations may be capsules, tablets, dragees, granules, inhalant, suppositories, solution, lotion, suspension, emulsion, ointment, gel, or the like. If desired, there may be included in these preparations, auxiliary substances, stabilizing agents, wetting or emulsifying agents, buffers and other commonly used additives.

In the pharmaceutical composition the compound (I) or a pharmaceutically acceptable salt thereof is included in an sufficient amount to have the desired effects of aforementioned pharmaceutical activities on the aforesaid diseases in human beings or animals.

While the dosage of therapeutically effective amount of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating the above-mentioned diseases. In general, amounts between 0.1 mg/body and about 1,000 mg/body may be administered per day.

The patents, patent applications and publications cited herein are incorporated by reference.

The following Preparations and Examples are given for the purpose of illustrating this invention.

Preparation 1

To acetic anhydride (20 ml) was added 70% nitric acid (2 ml) dropwise in an ice-bath. During the addition, the internal temperature of the mixture temporarily rose to 25° C. and dropped to 0° C. To the mixture was added 1-(4-methoxyphenyl)-5-[4-(methylsulfonyl)phenyl]-3-(trifluoromethyl)pyrazole (2.0 g) portionwise. The reaction mixture was allowed to stir for 5 hours and poured into ice-water. The precipitate formed was collected by filtration and dried to give 1-(4-methoxy-3-nitrophenyl)-5-[4-(methylsulfonyl)phenyl]-3-(trifluoromethyl)pyrazole (2.15 g).

An analytical sample was prepared by recrystallization from ethanol.

Mp: 175–177° C. (ethanol) IR (KBr): 1540, 1361, 1313, 1160, 1141 $cm^{-1}$ NMR (DMSO-$d_6$, δ): 3.25 (3H, s), 3.96 (3H, s), 7.39 (1H, s), 7.44 (1H, d, J=8 Hz), 7.5–7.7 (2H, m), 7.65 (1H, dd, J=2, 8 Hz), 7.9–8.0 (2H, m), 8.09 (1H, d, J=2 Hz)

MASS: 442 $(M+H)^+$

Preparation 2

A mixture of 1-(4-methoxy-3-nitrophenyl)-5-[4-(methylsulfonyl)-phenyl]-3-3-(trifluoromethyl)pyrazole (2.15 g), activated carbon (2.15 g), anhydrous iron(III) chloride (100 mg), hydrazine monohydrate (2.2 ml), ethanol (75 ml), and tetrahydrofuran (75 ml) was refluxed for 3.5 hours. The reaction mixture was filtered and the filtrate was concentrated in vacuo. The residue was purified by column chromatography on silica gel (gradient elution; 10:1 chloroform-ethyl acetate to 100:10:1 chloroform-ethyl acetate-methanol) to give the product, which was dissolved in ethyl acetate (10 ml) and treated with a solution of 4N hydrogen chloride in ethyl acetate (5 ml). The resultant solid was collected by filtration to give 1-(3-amino-4-methoxyphenyl)-5-[4-(methylsulfonyl)phenyl]-3-(trifluoromethyl)-pyrazole hydrochloride (1.92 g).

mp: 214–220° C. (ethanol) IR (KBr): 3424, 2003, 1631, 1313, 1160, 1157, 1132 $cm^{-1}$ NMR (DMSO-$d_6$, δ): 3.26 (3H, s), 3.87 (3H, s), 5.0–7.0 (3H, br m), 6.98 (1H, dd, J=2, 8 Hz), 7.09 (1H, d, J=8 Hz), 7.23 (1H, d, J=2 Hz), 7.34 (1H, s), 7.5–7.6 (2H, m), 7.9–8.0 (2H, m)

MASS: 412 $(M+H)^+$

Preparation 3

A solution of sodium nitrite (6 g) in water (50 ml) was added dropwise to a solution of 3-chloro-4-methoxyaniline (10 g) in concentrated hydrochloric acid (30 ml) at 0° C. with stirring. After the addition was completed, the reaction mixture was stirred at the same temperature for 1 hour. A solution of stannous chloride dihydrate (50 g) in concentrated hydrochloric acid (30 ml) was added dropwise at 0° C.

The resulting mixture was stirred for 2 hours at the same temperature. The resulting precipitate was collected by filtration, washed with ice water and dried in vacuo at 50° C. to afford (3-chloro-4-methoxyphenyl)hydrazine hydrochloride (11.5 g) as a yellow brown solid.

mp: 240–250° C. (decomp.) IR (Nujol): 3200, 2700, 1600, 1570, 1505, 1290 cm$^{-1}$ NMR (DMSO-d$_6$, δ): 3.80 (3H, s), 6.98 (1H, dd, J=2.7, 8.9 Hz), 7.09–7.17 (2H, m), 8.12 (1H, br s), 10.14 (3H, br s)

MASS: 173 (M+H)$^+$

Preparation 4

The mixture containing 4,4-difluoro-1-[(4-methylthio)phenyl]-butane-1,3-dione (1.0 g), (3-chloro-4-methoxyphenyl)hydrazine hydrochloride (0.94 g) and acetic acid (20 ml) was stirred at 100–110° C. After 2 hours, the reaction mixture was concentrated in vacuo. The resultant residue was partitioned between ethyl acetate and water. The organic layer was separated, washed with water and dried over magnesium sulfate. Evaporation of the solvent under reduced pressure gave 1-(3-chloro-4-methoxyphenyl)-3-(difluoromethyl)-5-[4-(methylthio)phenyl]pyrazole (2.10 g) as an oil.

NMR (CDCl$_3$, δ): 2.48 (3H, s), 3.91 (3H, s), 6.75–7.26 (2H, m), 6.69 (1H, s), 7.13 (2H, d, J=8.0 Hz), 7.18 (2H, d, J=8.0 Hz), 7.45 (1H, d, J=2.5 Hz)

MASS: 381 (M+H)$^+$

Preparation 5

The following compounds described in (1) to (11) were obtained according to a similar manner to that of Example 2.

(1) Ethyl 1-(4-fluoro-3-methylphenyl)-5-[4-(methylsulfonyl)-phenyl]pyrazole-3-carboxylate IR (KBr): 3008, 1712, 1309, 1224, 1153 cm$^{-1}$ NMR (CDCl$_3$, δ): 1.43 (3H, t, J=7.1 Hz), 2.28 (3H, d, J=1.6 Hz), 3.07 (3H, s), 4.47 (2H, q, J=7.1 Hz), 6.95–7.00 (2H, m), 7.13 (1H, s), 7.31 (1H, d, J=7.0 Hz), 7.42 (2H, d, J=8.6 Hz), 7.90 (2H, d, J=8.6 Hz)

MASS: 403 (M+H)$^+$ (2) Ethyl 1-(4-chloro-3-methylphenyl)-5-[4-(methylsulfonyl)-phenyl]pyrazole-3-carboxylate IR (KBr): 3127, 3000, 1710, 1313, 1234, 1151 cm$^{-1}$ NMR (CDCl$_3$, δ): 1.43 (3H, t, J=7.1 Hz), 2.38 (3H, s), 3.08 (3H, s), 4.47 (2H, q, J=7.1 Hz), 6.93 (1H, dd, J=8.4, 2.3 Hz), 7.30 (1H, d, J=8.4 Hz), 7.37 (1H, d, J=2.3 Hz), 7.43 (2H, d, J=8.6 Hz), 7.92 (2H, d, J=8.6 Hz)

MASS: 419 (M+H)$^+$ ($^{35}$Cl), 421 (M+H)$^+$ ($^{37}$Cl)

(3) Ethyl 1-(4-bromo-3-methylphenyl)-5-[4-(methylsulfonyl)-phenyl]pyrazole-3-carboxylate IR (KBr): 3126, 3004, 1710, 1315, 1234, 1153 cm$^{-1}$ NMR (CDCl$_3$, δ): 1.43 (3H, t, J=7.1 Hz), 2.40 (3H, s), 3.08 (3H, s), 4.47 (2H, q, J=7.1 Hz), 6.84 (1H, dd, J=8.4, 2.6 Hz), 7.13 (1H, s), 7.37–7.47 (3H, m), 7.49 (1H, d, J=8.4 Hz), 7.92 (2H, d, J=8.5 Hz)

MASS: 463 (M+H)$^+$ ($^{79}$Br), 465 (M+H)$^+$ ($^{81}$Br)

(4) Ethyl 1-(4-fluoro-3-methoxyphenyl)-5-[4-(methyl-sulfonyl)phenyl]pyrazole-3-carboxylate IR (KBr): 3004, 2923, 1714, 1313, 1263, 1224, 1155 cm$^{-1}$ NMR (CDCl$_3$, δ): 1.44 (3H, t, J=7.1 Hz), 3.08 (3H, s), 3.85 (3H, s), 4.47 (2H, q, J=7.1 Hz), 6.71 (1H, m), 6.98–7.14 (3H, m), 7.43 (2H, d, J=8.5 Hz), 7.92 (2H, d, J=8.5 Hz)

MASS: 419 (M+H)$^+$ (5) Ethyl 1-(4-chloro-3-methoxyphenyl)-5-[4-(methyl-sulfonyl)phenyl]pyrazole-3-carboxylate IR (KBr): 2981, 1722, 1311, 1251, 1220, 1153 cm$^{-1}$ NMR (CDCl$_3$, δ): 1.44 (3H, t, J=7.1 Hz), 3.08 (3H, s), 3.85 (3H, s), 4.47 (2H, q, J=7.1 Hz), 6.68 (1H, dd, J=8.4, 2.3 Hz), 7.05 (1H, d, J=2.3 Hz), 7.14 (1H, s), 7.31 (1H, d, J=8.4 Hz), 7.44 (2H, d, J=8.6 Hz), 7.92 (2H, d, J=8.6 Hz)

(6) Ethyl 1-(4-bromo-3-methoxyphenyl)-5-[4-(methylsulfonyl)-phenyl]pyrazole-3-carboxylate IR (KBr): 2979, 1724, 1311, 1251, 1220, 1151 cm$^{-1}$ NMR (CDCl$_3$, δ): 1.44 (3H, t, J=7.1 Hz), 3.08 (3H, s), 3.84 (3H, s), 4.47 (2H, q, J=7.1 Hz), 6.62 (1H, dd, J=8.4, 2.2 Hz), 7.01 (1H, s), 7.08–7.51 (4H, m), 7.92 (2H, d, J=8.2 Hz)

MASS: 479 (M+H)$^+$ ($^{79}$Br), 481 (M+H)$^+$ ($^{81}$Br)

(7) Ethyl 1-(3-fluoro-4-methylphenyl)-5-[4-(methylsulfonyl)-phenyl]pyrazole-3-carboxylate IR (KBr): 3002, 1714, 1313, 1276, 1241, 1189, 1151 cm$^{-1}$ NMR (CDCl$_3$, δ): 1.43 (3H, t, J=7.1 Hz), 2.31 (3H, d, J=1.8 Hz), 3.08 (3H, s), 4.46 (2H, q, J=7.1 Hz), 6.93 (1H, dd, J=8.3, 2.0 Hz), 7.08 (1H, dd, J=9.5, 2.0 Hz), 7.13 (1H, s), 7.20 (1H, d, J=8.3 Hz), 7.42 (2H, d, J=8.5 Hz), 7.91 (2H, d, J=8.5 Hz)

MASS: 403 (M+H)$^+$ (8) Ethyl 1-(3-chloro-4-methylphenyl)-5-[4-(methylsulfonyl)-phenyl]pyrazole-3-carboxylate IR (KBr): 3000, 1712, 1313, 1232, 1151 cm$^{-1}$ NMR (CDCl$_3$, δ): 1.43 (3H, t, J=7.1 Hz), 2.41 (3H, s), 3.08 (3H, s), 4.47 (2H, q, J=7.1 Hz), 6.98 (1H, dd, J=8.1, 2.2 Hz), 7.13 (1H, s), 7.20 (1H, d, J=8.1 Hz), 7.43 (2H, d, J=8.6 Hz), 7.47 (1H, d, J=2.2 Hz), 7.92 (2H, d, J=8.6 Hz)

MASS: 419 (M+H)$^+$ ($^{35}$Cl), 421 (M+H)$^+$ ($^{37}$Cl)

(9) Ethyl 1-(3-bromo-4-methylphenyl)-5-[4-(methylsulfonyl)-phenyl]pyrazole-3-carboxylate IR (KBr): 2983, 1718, 1311, 1232, 1153 cm$^{-1}$ NMR (CDCl$_3$, δ): 1.43 (3H, t, J=7.1 Hz), 2.43 (3H, s), 3.08 (3H, s), 4.47 (2H, q, J=7.1 Hz), 7.01 (1H, dd, J=8.1, 2.2 Hz), 7.12 (1H, s), 7.20 (1H, d, J=8.1 Hz) 7.43 (2H, d, J=8.6 Hz), 7.66 (1H, d, J=2.2 Hz), 7.92 (2H, d, J=8.6 Hz)

MASS: 463 (M+H)$^+$ ($^{79}$Br), 465 (M+H)$^+$ ($^{81}$Br)

(10) Ethyl 1-(3-fluoro-4-methoxyphenyl)-5-[4-(methyl-sulfonyl)phenyl]pyrazole-3-carboxylate IR (KBr): 3012, 2987, 1700, 1311, 1278, 1230, 1147 cm$^{-1}$ NMR (CDCl$_3$, δ): 1.43 (3H, t, J=7.1 Hz), 3.08 (3H, s), 3.92 (3H, s), 4.47 (2H, q, J=7.1 Hz) , 6.89 (1H, d, J=8.9 Hz), 6.99 (1H, dd, J=8.9, 2.3 Hz), 7.11–7.26 (2H, m), 7.43 (2H, d, J=8.5 Hz), 7.91 (2H, d, J=8.5 Hz)

MASS: 419 (M+H)$^+$

(11) Ethyl 1-(3-chloro-4-methoxyphenyl)-5-[4-(methyl-sulfonyl)phenyl]pyrazole-3-carboxylate IR (KBr): 2979, 1718, 1313, 1272, 1226, 1151 cm$^{-1}$ NMR (CDCl$_3$, δ): 1.43 (3H, t, J=7.1 Hz), 3.08 (3H, s), 3.93 (3H, s), 4.47 (2H, q, J=7.1 Hz), 6.87 (1H, d, J=8.8 Hz), 7.06 (1H, dd, J=8.8, 2.6 Hz), 7.12 (1H, s), 7.43 (2H, d, J=8.5 Hz), 7.50 (1H, d, J=2.6 Hz), 7.91 (2H, d, J=8.5 Hz)

MASS: 435 (M+H)$^+$ ($^{35}$Cl), 437 (M+H)$^+$ ($^{37}$Cl)

Preparation 6

The following compound was obtained according to a similar manner to that of Preparation 1.

1-(4-Methoxy-3-nitrophenyl)-5-[4-(methylsulfonyl)-phenyl]pyrazole-3-carbonitrile IR (KBr): 3072, 3021, 2242, 1535, 1363, 1311, 1282, 1151 cm$^{-1}$ NMR (CDCl$_3$, δ): 3.10 (3H, s), 4.02 (3H, s), 6.98 (1H, s), 7.12 (1H, d, J=9.1 Hz), 7.41–7.48 (3H, m), 7.81 (1H, d, J=2.7 Hz), 7.99 (2H, d, J=8.5 Hz)

MASS: 399 (M+H)$^+$

Preparation 7

A mixture of 1-(4-methoxy-3-nitrophenyl)-5-[4-(methylsulfonyl)-phenyl]pyrazole-3-carbonitrile (1.8 g) and ammonium chloride (0.18 g) in ethanol-water (50 ml) was stirred under 90° C. After several minutes, iron (powder) (1.8 g) was added and the resulting mixture was stirred for 1.5 hours at same temperature. After cooling, the insoluble material was filtrated off and washed with tetrahydrofuran. The filtrate was concentrated under reduced pressure to give a material which on treatment with 4N hydrogen chloride in ethyl acetate afforded 1-(3-amino-4-methoxyphenyl)-5-[4-(methylsulfonyl)-phenyl]pyrazole-3-carbonitrile hydrochloride (1.8 g).

IR (KBr): 3400, 2842, 2244, 1303, 1282, 1147 cm$^{-1}$ NMR (DMSO-d$_6$, δ): 3.25 (3H, s), 3.86 (3H, s), 6.86 (1H, dd, J=8.6, 2.0 Hz), 7.03 (1H, d, J=8.6 Hz), 7.05 (1H, d, J=2.0 Hz), 7.55 (2H, d, J=8.4 Hz), 7.94 (2H, d, J=8.4 Hz)

MASS: 369 (M+H)$^+$

Preparation 8

To a mixture of (3-methoxyphenyl)hydrazine (6 g) and 3-[4-(methylthio)phenyl]acrylonitrile (5.7 g) in methanol (100 ml) was added sodium methoxide (28 wt. % solution in methanol) (18 ml) at ambient temperature. The mixture was heated to dryness under nitrogen at 140° C. for 30 minutes. The resultant orange mass was partitioned between dichloromethane and ice water. The organic layer was dried over magnesium sulfate, and then filtered. This filtrate was evaporated in vacuo. The resultant mass was dissolved in ethyl acetate (150 ml) and refluxed for 1 hour in the presence of magnesium (IV) oxide (20 g). This mixture was cooled, and filtered. The filtrate was evaporated in vacuo. The resultant mass was purified by column chromatography on silica gel using dichloromethane as eluent to give {1-(3-methoxyphenyl)-5-[4-(methylthio)-phenyl]pyrazol-3-yl}amine (5.2 g).

IR (Nujol): 3450, 3320, 3220, 1630, 1600 cm$^{-1}$ NMR (DMSO-d$_6$, δ): 2.47 (3H, s), 3.66 (3H, s), 4.98 (2H, s), 5.81 (1H, s), 6.61–6.79 (3H, m), 7.12–7.25 (4H, m)

MASS: 312 (M+H)$^+$

Preparation 9

The following compounds described in (1) to (11) were obtained according to a similar manner to that of Preparation 8.

(1) {1-(4-Fluoro-3-methylphenyl)-5-[4-(methylthio)phenyl]pyrazol-3-yl}amine

NMR (DMSO-d$_6$, δ): 2.18 and 2.19 (total 3H, s), 2.45 (3H, s), 4.92 (2H, s), 5.81 (1H, s), 6.80–6.88 (1H, s), 7.02–7.23 (6H, m)

IR (KBr): 3303, 3205, 1625, 1563, 1508 cm$^{-1}$ MASS: 300 (M+H)$^+$ (2) {1-(4-Chloro-3-methylphenyl)-5-[4-(methylthio)phenyl]pyrazol-3-yl}amine IR (Nujol): 1630, 1600 cm$^{-1}$ NMR (DMSO-d$_6$, δ): 2.27 (3H, s), 2.47 (3H, s), 5.00 (2H, s), 5.83 (1H, s), 6.70–6.85 (1H, m) , 7.11–7.39 (6H, m)

MASS: 330 (M+H)$^+$ (3) {1-(4-Bromo-3-methylphenyl)-5-[4-(methylthio)phenyl]pyrazol-3-yl}amine IR (Nujol): 3450, 1630 cm$^{-1}$ NMR (DMSO-d$_6$, δ): 2.29 (3H, s), 2.47 (3H, s), 5.00 (2H, s), 5.83 (1H, s), 6.71–6.77 (1H, m), 7.14 (2H, d, J=8.5 Hz), 7.23 (2H, d, J=8.5 Hz), 7.29 (1H, d, J=1.6 Hz) , 7.46 (1H, d, J=8.6 Hz)

MASS: 375 (M+H)$^+$ (4) {1-(4-Chloro-3-methoxyphenyl)-5-[4-(methylthio)phenyl]pyrazol-3-yl}amine IR (Nujol): 3450, 3300, 3200, 1630, 1600 cm$^{-1}$ NMR (DMSO-d$_6$, δ): 2.47 (3H, s), 3.70 (3H, s), 5.06 (2H, s), 5.83 (1H, s), 6.59 (1H, dd, J=8.5, 2.3 Hz), 6.98 (1H, d, J=2.3 Hz), 7.16 (2H, d, J=8.6 Hz), 7.26 (2H, d, J=8.6 Hz), 7.31 (2H, d, J=8.5 Hz)

MASS: 346 (M+H)$^+$ (5) {1-(3-Fluoro-4-methylphenyl)-5-[4-(methylthio)phenyl]pyrazol-3-yl}amine IR (KBr): 3295, 3195, 1625, 1513 cm$^{-1}$ NMR (DMSO-d$_6$, δ): 2.19 (3H, s), 2.47 (3H, s), 5.02 (2H, s), 5.82 (1H, s), 6.80 (1H, dd, J=8.1, 1.9 Hz), 6.96 (1H, dd, J=11.1, 1.9 Hz), 7.12–7.25 (5H, m)

MASS: 314 (M+H)$^+$ (6) {1-(3-Chloro-4-methylphenyl)-5-[4-(methylthio)phenyl]pyrazol-3-yl}amine IR (Nujol): 3450, 3400, 3200, 1630, 1610 cm$^{-1}$ NMR (DMSO-d$_6$, δ): 2.29 (3H, s), 2.47 (3H, s), 5.03 (2H, s), 5.82 (1H, s), 6.89 (1H, dd, J=8.2, 2.1 Hz), 7.13–7.27 (6H, m)

MASS: 330 (M+H)$^+$ (7) {1-(3-Bromo-4-methylphenyl)-5-[4-(methylthio)phenyl]pyrazol-3-yl}amine This compound was used in the next reaction without purification.

(8) {1-(3-Chloro-4-methoxyphenyl)-5-[4-(methylthio)phenyl]pyrazol-3-yl}amine

IR (Nujol): 3450, 3300, 3200, 1645 cm$^{-1}$ NMR (DMSO-d$_6$, δ): 2.47 (3H, s), 2.50 (3H, s), 4.95 (2H, s), 5.80 (1H, s), 6.96–7.28 (7H, m)

MASS: 346 (M+H)$^+$ (9) {1-(4-Ethylphenyl)-5-[4-(methylthio)phenyl]pyrazol-3-yl}amine crystals mp: 128–132° C. IR (Nujol): 3490, 3460, 1620, 1600 cm$^{-1}$ NMR (DMSO-d$_6$, δ): 1.13–1.23 (3H, m), 2.54 (3H, s), 2.52–2.64 (2H, m), 4.91 (2H, br s), 5.79 (1H, s), 7.03–7.56 (8H, m)

MASS: 309 (M+H)$^+$

(10) {5-[4-(Methylthio)phenyl]-1-(4-n-propylphenyl)-pyrazol-3-yl}amine crystals mp: 140–1420° C. IR (KBr): 3450, 3303, 3193, 1630, 1515 cm$^{-1}$ NMR (DMSO-d$_6$, δ): 0.88 (3H, t, J=7 Hz), 1.51–1.63 (2H, m), 2.46 (3H, s), 2.49–2.52 (2H, m), 4.92 (2H, br s), 5.79 (1H, s), 7.01–7.22 (8H, m)

MASS: 324 (M+H)$^+$

(11) {1-(4-Isopropylphenyl)-5-[4-(methylthio)phenyl]pyrazol-3-yl}amine crystals mp: 148–150° C. IR (KBr): 3450, 3305, 3197, 1631, 1513 cm$^{-1}$ NMR (DMSO-d$_6$, δ): 1.18 (6H, d, J=7 Hz), 2.46 (3H, s), 2.83–2.91 (1H, m), 4.92 (2H, br s), 5.79 (1H, s), 7.01–7.22 (8H, m)

MASS: 324 (M+H)+

Preparation 10

The following compounds described in (1) to (2) were obtained according to a similar manner to that of Preparation 3.

(1) (4-Fluoro-3-methylphenyl)hydrazine hydrochloride

IR (KBr): 3002, 1585, 1550 cm$^{-1}$ NMR (DMSO-d$_6$, δ): 2.18 (3H, s), 6.8–7.15 (3H, m)

(2) (3-Fluoro-4-methylphenyl)hydrazine hydrochloride

IR (KBr): 2994, 1631, 1585, 1515 cm$^{-1}$ NMR (DMSO-d$_6$, δ): 2.13 (3H, s), 6.70–6.86 (2H, m), 7.16 (1H, t, J=8.5 Hz)

Preparation 11

To a solution of 3-chloro-1-(3-methoxyphenyl)-5-[4-(methylsulfonyl)phenyl]pyrazole (575 mg) in acetic anhydride (10 ml) and acetic acid (1 ml) was added nitric acid (fuming) (500 ml) at 0° C. After being stirred at 0° C. for 2 hours, the reaction mixture was poured into water, and extracted with dichloromethane. The organic layer was dried over magnesium sulfate, and filtered. The filtrate was evaporated in vacuo, and purified by column chromatography using dichloromethane as eluent to give 3-chloro-1-(3-methoxy-4-nitro-phenyl)-5-[4-(methylsulfonyl)phenyl] pyrazole (590 mg).

mp: 170–175° C. IR (Nujol): 1615, 1590 cm$^{-1}$ NMR (DMSO-d$_6$, δ): 3.26 (3H, s), 3.80 (3H, s), 6.95 (1H, dd, J=8.7, 2.1 Hz), 7.34 (1H, d, J=2.0 Hz), 7.60 (2H, d, J=8.4 Hz), 7.95 (2H, d, J=8.6 Hz), 7.97 (2H, d, J=8.4 Hz)

MASS: 408 (M+H)+

Preparation 12

To a solution of 3-chloro-1-(3-methoxy-4-nitrophenyl)-5-[4-(methylsulfonyl)phenyl]pyrazole (900 mg) in ethanol (30 ml) and tetrahydrofuran (30 ml) were added active carbon (3 g), hydrazine monohydrate (2 ml) and ferric chloride (50 mg). The mixture was refluxed for 2 hours, and filtered. The filtrate was evaporated in vacuo and partitioned between water and dichloromethane. The organic layer was dried over magnesium sulfate and filtered. The filtrate was evaporated in vacuo to give 1-(4-amino-3-methoxyphenyl)-3-chloro-5-[4-(methylsulfonyl)phenyl]pyrazole (820 mg).

IR (Nujol): 3350, 1630, 1600 cm$^{-1}$NMR (DMSO-d$_6$, δ): 3.23 (3H, s), 3.83 (3H, s), 5.08 (2H, s), 6.56 (2H, s), 6.81 (1H, s), 6.90 (1H, s), 7.51 (2H, d, J=8.3 Hz), 7.90 (2H, d, J=8.3 Hz)

MASS: 378 (M+H)+

Preparation 13

A mixture of 2-methoxy-5-nitrobenzonitrile (14 g), ammonium chloride (5 g), the powder of reduced iron (9 g) in methanol was refluxed for 4 hours and cooled. The reaction mixture was filtered and the filtrate was poured into water. The resultant precipitates were filtered and washed with water to give 3-cyano-4-methoxyaniline (7.7 g).

IR (KBr): 3420, 3320, 2220 cm$^{-1}$ NMR (DMSO-d$_6$, δ): 3.76 (3H, s), 5.05 (2H, br s), 6.79 (1H, d, J=2.7 Hz), 6.86 (1H, dd, J=8.9, 2.7 Hz), 6.96 (1H, d, J=8.9 Hz)

MASS: 149 (M+H)+

Preparation 14

A solution of sodium nitrite (4.0 g) in water (7 ml) was added to an ice cooled mixture of 3-cyano-4-methoxyaniline (7.7 g) and concentrated hydrochloric acid (21 ml). The mixture was stirred at 0° C. for 30 minutes. To the resultant mixture a solution of tin(II) chloride dihydrate (49 g) and concentrated hydrochloric acid (5 ml) was added at 0° C. and stirred for 1 hour. The precipitates were filtered and washed with ice cooled concentrated hydrochloric acid (10 ml) to give crude (3-cyano-4-methoxyphenyl)hydrazine hydrochloride (14.8 g).

NMR (DMSO-d$_6$, δ): 3.87 (3H, s), 7.24 (1H, d, J=10.0 Hz), 7.30–7.37 (2H, comp. m), 8.27 (1H, br s), 10.15 (3H, br s)

Preparation 15

A stirred mixture of (3-cyano-4-methoxyphenyl) hydrazine hydrochloride (3.7 g), 3-[4-(methylthio)phenyl] acrylonitrile (2.3 g) and sodium methoxide (0.9 g) in methanol 13 ml was gradually heated to 140° C. under atmospheric pressure and N$_2$ atmosphere, and continued to heat for 8 hours at 140° C. Ethyl acetate and water were added to the reaction mixture. The organic layer was separated, washed with brine, dried over magnesium sulfate, and concentrated under reduced pressure to give crude 1-(3-cyano-4-methoxyphenyl)-5-[4-(methylthio)-phenyl]-2-pyrazoline-3-amine (4.0 g).

Preparation 16

A mixture of 1-(3-cyano-4-methoxyphenyl)-5-[4-(methylthio)phenyl]-2-pyrazoline-3-amine (4.0 g) and manganese(IV) oxide (6.0 g) in toluene (100 ml) was stirred at ambient temperature for 8 hours. The insoluble material was filtered and washed with ethyl acetate. The resulting solution was concentrated under reduced pressure. The residue was subjected to column chromatography on silica gel eluting with a mixture of acetone and dichloromethane (1:1) to give partially purified 1-(3-cyano-4-methoxyphenyl)-5-[4-(methylthio)phenyl]pyrazole-3-amine (1.1 g).

IR (KBr): 2225 cm$^{-1}$

Preparation 17

A solution of sodium nitrite (0.36 g) in water (0.5 ml) was added to an ice cooled mixture of 1-(3-cyano-4-methoxyphenyl)-5-[4-(methylthio)phenyl]pyrazol-3-amine (1.08 g), concentrated hydrochloric acid (15 ml) and acetic acid (35 ml). The mixture was stirred at 0° C. for 30 minutes and added portionwise to a mixture of cuprous chloride (1.37 g) and concentrated hydrochloric acid (10 ml) at ambient temperature. The mixture was refluxed for 1 hour, poured into water and extracted with toluene. The extract was washed with water, dried over magnesium sulfate, and concentrated under reduced pressure. The resulting residue was purified by column chromatography on silica gel eluting with toluene to give 3-chloro-1-(3-cyano-4-methoxyphenyl)-5-[4-(methylthio)phenyl]pyrazole (0.29 g).

IR (Film): 2230, 1600, 1500 cm$^{-1}$ NMR (CDCl$_{13}$, δ): 2.49 (3H, s), 3.95 (3H, s), 6.41 (1H, s), 6.92 (1H, d, J=9.0 Hz), 7.09 (2H, d, J=8.6 Hz), 7.19 (2H, d, J=8.6 Hz), 7.42 (1H, dd, J=9.0, 2.7 Hz), 7.54 (1H, d, J=2.7 Hz)

MASS: 356 (M+H)+

Preparation 18

The following compounds described in (1) to (3) were obtained according to a similar manner to that of Preparation 11.

(1) 3-Chloro-1-(4-ethyl-3-nitrophenyl)-5-[4-(methylsulfonyl)phenyl]pyrazole crystals mp: 134–135° C. IR (KBr): 1577 cm$^{-1}$ NMR (DMSO-d$_6$, δ): 1.21 (3H, t, J=7 Hz), 2.84 (2H, q, J=7 Hz), 3.25 (3H, s), 7.02 (1H, s), 7.48–7.61 (4H, m), 7.89–7.94 (3H, m)

MASS: 406 (M+H)+ ($^{35}$Cl), 408 (M+H)+ ($^{37}$Cl)

(2) 3-Chloro-5-[4-(methylsulfonyl)phenyl]-1-(3-nitro-4-n-propylphenyl)pyrazole crystals mp: 42–46° C. IR (KBr): 1535 cm$^{-1}$ NMR (DMSO-d$_6$, δ): 0.91 (3H, t, J=7 Hz), 1.54–1.65 (2H, m), 2.79 (2H, t, J=7 Hz), 3.25 (3H, s), 7.07 (1H, s), 7.46–7.61 (4H, m), 8.27–8.32 (3H, m)

MASS: 420 (M+H)+

(3) 1-(4-Isopropyl-3-nitrophenyl)-5-[4-(methylsulfonyl)phenyl]-3-(trifluoromethyl)pyrazole crystals mp: 64–69° C. IR (KBr): 1536 cm$^{-1}$ NMR (DMSO-d$_6$, δ): 1.25 (6H, d, J=7 Hz), 3.20 (1H, m), 3.27 (3H, s), 7.42 (1H, s), 7.76–7.59 (4H, m), 7.89 (2H, d, J=9 Hz), 7.97 (1H, s)

MASS: 454 (M+H)+

Preparation 19

The following compounds described in (1) to (3) were obtained according to a similar manner to that of Preparation 12.

(1) 1-(3-Amino-4-ethylphenyl)-3-chloro-5-[4-(methylsulfonyl)phenyl]pyrazole crystals mp: 158–160° C. IR (KBr): 3462, 3442, 3351 cm$^{-1}$ NMR (DMSO-d$_6$, δ): 1.30 (3H, t, J=7 Hz), 2.43 (2H, q, J=7 Hz), 3.24 (3H, s), 5.19 (2H, br s), 6.30 (1H, dd, J=8, 2 Hz), 6.62 (1H, d, J=2 Hz), 6.8–6.9 (2H, m), 7.52 (2H, d, J=8 Hz), 7.91 (2H, d, J=8 Hz)

MASS: 376 (M+H)+

(2) 1-(3-Amino-4-n-propylphenyl)-3-chloro-5-[4-(methylsulfonyl)-phenyl]pyrazole crystals mp: 152–154° C. IR (KBr): 3461, 3350, 1628, 1595 cm$^{-1}$ NMR (DMSO-d$_6$, δ): 0.92 (3H, t, J=7 Hz), 1.48–1.59 (2H, m), 2.41 (2H, t, J=7 Hz), 3.60 (3H, s), 5.19 (2H, br s), 6.27 (1H, dd, J=8, 2 Hz), 6.61 (1H, d, J=2 Hz), 6.12–6.57 (2H, m), 7.51 (2H, d, J=8 Hz), 7.90 (2H, d, J=8 Hz)

MASS: 390 (M+H)+

(3) 1-(3-Amino-4-isopropylphenyl)-5-[4-(methylsulfonyl)phenyl]-3-(trifluoromethyl)pyrazole crystals mp: 134–135° C. IR (KBr): 3430, 3359, 1635, 1506 cm$^{-1}$ NMR (DMSO-d$_6$, δ): 1.14 (6H, d, J=7 Hz), 2.97 (1H, m), 3.26 (3H, s), 5.29 (1H, br s), 6.37 (1H, dd, J=8, 2 Hz), 6.69 (1H, d, J=2 Hz), 7.03 (1H, d, J=8 Hz), 7.31 (1H, s), 7.58 (2H, d, J=9 Hz), 7.93 (2H, d, J=9 Hz)

MASS: 424 (M+H)+

Preparation 20

Into a 1 l round bottom flask were added cupric chloride (anhydrous) (7.77 g), acetonitrile (150 ml), lithium chloride (anhydrous) (6.13 g) and n-butyl nitrate (4.47 g) at 20 to 25° C. under nitrogen gas. While stirring, {1-(3-chloro-4-methoxyphenyl)-5-[4-(methylthio)phenyl]pyrazol-3-yl}amine (10.0 g) was added for 30 minutes at the same temperature. The reaction mixture was stirred for 2 hours and then refluxed for additional 2 hours. After the reaction was completed, 1N hydrochloric acid (325 ml) and ethyl acetate (150 ml) were added for quenching. The organic layer was separated and washed with brine (180 ml) and then evaporated to give a crude object compound as an oil, which was purified by silica gel column chromatography (SiO$_2$ 50 g, toluene:n-heptane=3:1), and evaporated to give a pure 3-chloro-1-(3-chloro-4-methoxyphenyl)-5-[4-(methylthio)phenyl]pyrazole (7.77 g).

NMR (CDCl$_3$, δ): 2.48 (3H, s), 3.91 (3H, s), 6.39 (1H, s), 6.80–7.44 (7H, m)

MASS: 365 (M+H)+

EXAMPLE 1

To a solution of 1-[4-(methylthio)phenyl]-4,4,4-trifluorobutane-1,3-dione (2 g) in acetic acid (30 ml) was added 3-tolylhydrazine hydrochloride (1.27 g). The mixture was refluxed for 2 hours. After cooling, the reaction mixture was poured into ice water and extracted with dichloromethane. The organic layer was dried over magnesium sulfate and filtered. The filtrate was evaporated in vacuo and the resultant oil was dissolved in methanol (100 ml). To this solution was added a solution of Oxone® (potassium peroxy monosulfate) (9.8 g) in water (20 ml) at room temperature. The mixture was stirred for 1 hour and then filtered. The filtrate was partitioned between water and dichloromethane. The organic layer was dried over magnesium sulfate and filtered. The filtrate was evaporated in vacuo and purified by column chromatography on silica gel using dichloromethane as eluent to give 1-(3-methylphenyl)-5-[4-(methylsulfonyl)phenyl]-3-(trifluoromethyl)pyrazole (1.98 g).

IR (Nujol): 1600 cm$^{-1}$ NMR (DMSO-d$_6$, δ): 2.33 (3H, s), 3.25 (3H, s), 7.06–7.13 (1H, m), 7.32–7.39 (4H, m), 7.56 (2H, d, J=6.7 Hz), 7.93 (2H, d, J=6.7 Hz)

MASS: 381 (M+H)+

EXAMPLE 2

A mixture of 1-[4-(methylsulfonyl)phenyl]-4,4,4-trifluorobutane-1,3-dione (620 mg) and (3-methyl-4-chlorophenyl)hydrazine hydrochloride (425 mg) in acetic acid (2 ml) was refluxed for 1 hour. After cooling, the solvent was poured into water (50 ml) and stirred for 30 minutes. The resulting precipitates were collected by filtration and washed with water and dried in vacuo. The residue was recrystallized from ethanol to afford 1-(4-chloro-3-methylphenyl)-5-[4-(methylsulfonyl)phenyl]-3-(trifluoromethyl)pyrazole (569 mg).

mp: 152.0–154.0° C. IR (KBr): 3128, 3070, 1317, 1286, 1238, 1161, 1128 cm$^{-1}$ NMR (CDCl$_3$, δ): 2.39 (3H, s), 3.08 (3H, s), 6.85 (1H, s), 6.92 (1H, dd, J=8.4, 2.7 Hz), 7.32 (1H, d, J=8.4 Hz), 7.33 (1H, d, J=2.7 Hz), 7.43 (2H, d, J=8.6 Hz), 7.93 (2H, d, J=8.6 Hz)

MASS: 415 (M+H)+ Elemental Analysis for C$_{18}$H$_{14}$ClF$_3$N$_2$O$_2$S Calcd. C, 52.12; H, 3.40; N, 6.75. Found C, 51.82; H, 3.30; N, 6.68.

EXAMPLE 3

The following compounds described in (1) to (18) were obtained in a similar manner to that of Example 2.

(1) 1-(4-Fluoro-3-methylphenyl)-5-[4-(methylsulfonyl)-phenyl]-3-(trifluoromethyl)pyrazole mp: 134–136° C. (ethanol) IR (KBr): 1602, 1315, 1222, 1160, 1157, 1130, 1101 cm$^{-1}$ NMR (DMSO-d$_6$, δ): 2.25 (3H, d, J=1 Hz), 3.25 (3H, s), 7.1–7.6 (2H, m), 7.37 (1H, s), 7.4–7.6 (3H, m), 7.9–8.0 (2H, m)

MASS: 339 (M+H)+

(2) 1-(4-Bromo-3-methylphenyl)-5-[4-(methylsulfonyl)phenyl]-3-(trifluoromethyl)pyrazole mp: 127.0–129.0° C. IR (KBr): 3134, 3093, 1315, 1238, 1165, 1128 cm$^{-1}$ NMR (CDCl$_3$, δ): 2.41 (3H, s), 3.09 (3H, s), 6.84 (1H, dd, J=8.4, 2.6 Hz), 6.85 (1H, s), 7.34 (1H, d, J=2.6 Hz), 7.44 (2H, d, J=8.6 Hz), 7.51 (1H, d, J=8.4 Hz), 7.94 (2H, d, J=8.6 Hz)

MASS: 459 (M+H)+ ($^{79}$Br), 461 (M+H)+ ($^{81}$Br) Elemental Analysis for C$_{18}$H$_{14}$BrF$_3$N$_2$O$_2$S Calcd. C, 47.07; H, 3.07; N, 6.10. Found C, 47.19; H, 3.05; N, 6.04.

(3) 1-(4-Fluoro-3-methoxyphenyl)-5-[4-(methylsulfonyl)-phenyl]-3-(trifluoromethyl)pyrazole mp: 159–160° C. (ethanol) IR (KBr): 1612, 1317, 1222, 1162, 1155, 1114 cm$^{-1}$ NMR (DMSO-d$_6$, δ): 3.25 (3H, s), 3.76 (3H, s), 6.8–7.0 (1H, m), 7.2–7.4 (2H, m), 7.38 (1H, s), 7.5–7.6 (2H, m), 7.9–8.0 (2H, m)

MASS: 415 (M+H)$^+$

(4) 1-(4-Chloro-3-methoxyphenyl)-5-[4-(methylsulfonyl)-phenyl]-3-(trifluoromethyl) pyrazole mp: 157–158° C. (ethanol) IR (KBr): 1596, 1592, 1315, 1307, 1114, 1106, 1101 cm$^{-1}$ NMR (DMSO-d$_6$, δ): 3.25 (3H, s), 3.74 (3H, s), 6.8–7.0 (1H, m), 7.2–7.3 (1H, m), 7.39 (1H, s), 7.4–7.7 (3H, m), 7.9–8.0 (2H, m)

MASS: 431 (M+H)$^+$

(5) 1-(4-Bromo-3-methoxyphenyl)-5-[4-(methylsulfonyl)-phenyl]-3-(trifluoromethyl) pyrazole mp: 156–157° C. (3:1 n-hexane-ethyl acetate) IR (KBr): 1592, 1313, 1162, 1157, 1133 cm$^{-1}$ NMR (DMSO-d$_6$, δ): 3.25 (3H, s), 3.75 (3H, s), 6.85 (1H, dd, J=2, 8 Hz), 7.20 (1H, d, J=2 Hz), 7.39 (1H, s), 7.5–7.7(3H, m), 7.9–8.0 (2H, m)

MASS: 475 (M+H)$^+$

(6) 1-(3-Fluoro-4-methylphenyl)-5-[4-(methylsulfonyl)-phenyl]-3-(trifluoromethyl) pyrazole mp: 158.0–160.0° C. IR (KBr): 3132, 3078, 1315, 1161, 1128 cm$^{-1}$ NMR (CDCl$_3$, δ): 2.31 (3H, d, J=1.9 Hz), 3.09 (3H, s), 6.84 (1H, s), 6.92 (1H, dd, J=8.1, 2.1 Hz), 7.05 (1H, d, J=9.7 Hz), 7.19 (1H, t, J=7.7 Hz), 7.44 (2H, d, J=8.5 Hz), 7.93 (2H, d, J=8.5 Hz)

MASS: 399 (M+H)$^+$ Elemental Analysis for C$_{18}$H$_{14}$F$_4$N$_2$O$_2$S Calcd. C, 54.27; H, 3.54; N, 7.03. Found C, 54.39; H, 3.48; N, 7.01.

(7) 1-(3-Chloro-4-methylphenyl)-5-[4-(methylsulfonyl)-phenyl]-3-(trifluoromethyl) pyrazole mp: 136.5–138.5° C. IR (KBr): 1315, 1236, 1163 cm$^{-1}$ NMR (CDCl$_3$, δ): 2.41 (3H, s), 3.08 (3H, s), 6.84 (1H, s), 6.98 (1H, dd, J=8.3, 2.2 Hz), 7.22 (1H, d, J=8.3 Hz), 7.42 (1H, s), 7.44 (2H, d, J=8.6 Hz), 7.94 (2H, d, J=8.6 Hz)

MASS: 415 (M+H)$^+$ ($^{35}$Cl), 417 (M+H)$^+$ ($^{37}$Cl) Elemental Analysis for C$_{18}$H$_{14}$ClF$_3$N$_2$O$_2$S.1/2H$_2$O Calcd. C, 51.01; H, 3.57; N, 6.61. Found C, 51.15; H, 3.26; N, 6.60.

(8) 1-(3-Bromo-4-methylphenyl)-5-[4-(methylsulfonyl)phenyl]-3-(trifluoromethyl)pyrazole mp: 159.0–161.° C. IR (KBr): 1313, 1234, 1162, 1147 cm$^{-1}$ NMR (CDCl$_3$, δ): 2.43 (3H, s), 3.08 (3H, s), 6.84 (1H, s), 7.02 (1H, dd, J=8.2, 2.2 Hz), 7.22 (1H, d, J=8.2 Hz), 7.44 (2H, d, J=8.6 Hz), 7.61 (1H, d, J=2.2 Hz), 7.94 (2H, d, J=8.6 Hz)

MASS: 459 (M+H)$^+$ ($^{79}$Br), 461 (M+H)$^+$ ($^{81}$Br) Elemental Analysis for C$_{18}$H$_{14}$BrF$_3$N$_2$O$_2$S.0.3H$_2$O Calcd. C, 46.53; H, 3.17; N, 6.03. Found C, 46.58; H, 2.95; N, 6.01.

(9) 1-(3-Fluoro-4-methoxyphenyl)-5-[4-(methylsulfonyl)-phenyl]-3-(trifluoromethyl) pyrazole mp: 178.5–180.5° C. IR (KBr): 3070, 3016, 1317, 1282, 1238, 1160, 1139, 1097 cm$^{-1}$ NMR (CDCl$_3$, δ): 3.09 (3H, s), 3.93 (3H, s), 6.84 (1H, s), 6.88–7.15 (3H, m), 7.43 (2H, d, J=8.6 Hz), 7.93 (2H, d, J=8.6 Hz)

MASS: 415 (M+H)$^+$ Elemental Analysis for C$_{18}$H$_{14}$F$_4$N$_2$O$_3$S Calcd. C, 52.17; H, 3.41; N, 6.76. Found C, 52.23; H, 3.42; N, 6.70.

(10) 1-(3-Chloro-4-methoxyphenyl)-5-[4-(methylsulfonyl)-phenyl]-3-(1trifluoromethyl) pyrazole mp: 184.0–186.° C. IR (KBr): 3016, 1315, 1280, 1228, 1159, 1137 cm$^{-1}$ NMR (CDCl$_3$, δ): 3.08 (3H, s), 3.94 (3H, s), 6.84 (1H, s), 6.88 (1H, d, J=8.6 Hz), 7.06 (1H, dd, J=8.6, 2.6 Hz), 7.44 (2H, d, J=8.6 Hz), 7.45 (1H, s), 7.93 (2H, d, J=8.6 Hz)

MASS: 431 (M+H)$^+$ ($^{35}$Cl), 433 (M+H)$^+$ ($^{37}$Cl) Elemental Analysis for C$_{18}$H$_{14}$ClF$_3$N$_2$O$_3$S.1/2H$_2$O Calcd. C, 49.15; H, 3.44; N, 6.37. Found C, 49.03; H, 3.18; N, 6.27.

(11) 3-(Difluoromethyl)-1-(4-fluoro-3-methylphenyl)-5-[4-(methylsulfonyl)phenyl] pyrazole mp: 154–155° C. (ethanol) IR (KBr): 1504, 1315, 1155 cm$^{-1}$ NMR (DMSO-d$_6$, δ): 2.24 (3H, d, J=1 Hz), 3.24 (3H, s), 7.12 (1H, s), 7.14 (1H, t, J=54 Hz), 7.0–7.3 (2H, m), 7.4–7.5 (1H, m), 7.5–7.6 (2H, m), 7.9–8.0 (2H, m)

MASS: 381 (M+H)$^+$

(12) 1-(4-Chloro-3-methylphenyl)-3-(difluoromethyl)-5-[4-(methylsulfonyl)phenyl] pyrazole mp: 145–146° C. (ethanol) IR (KBr): 1600, 1315, 1153 cm$^{-1}$ NMR (DMSO-d$_6$, δ): 2.34 (3H, s), 3.25 (3H, s), 7.08 (1H, dd, J=2, 8 Hz), 7.11 (1H, s), 7.13 (1H, t, J=54 Hz), 7.44 (1H, d, J=8 Hz), 7.50 (1H, d, J=2 Hz), 7.5–7.6 (2H, m), 7.9–8.0 (2H, m)

MASS: 397 (M+H)$^+$

(13) 1-(4-Bromo-3-methylphenyl)-3-(difluoromethyl)-5-[4-(methylsulfonyl)phenyl] pyrazole mp: 141–142° C. (ethanol) IR (KBr): 1598, 1307, 1147 cm$^{-1}$ NMR (DMSO-d$_6$, δ): 2.35 (3H, s), 3.25 (3H, s), 6.99 (1H, dd, J=2, 8 Hz), 7.13 (1H, s), 7.15 (1H, t, J=54 Hz), 7.50 (1H, d, J=8 Hz), 7.5–7.6 (2H, m), 7.64 (1H, d, J=2 Hz), 7.9–8.0 (2H, m)

MASS: 441 (M+H)$^+$

(14) 3-(Difluoromethyl)-1-(3-fluoro-4-methylphenyl)-5-[4-(methylsulfonyl)phenyl] pyrazole mp: 161–162° C. (ethanol) IR (KBr): 1625, 1594, 1313, 1157 cm$^{-1}$ NMR (DMSO-d$_6$, δ): 2.26 (3H, d, J=1 Hz), 3.25 (3H, s), 7.03 (1H, dd, J=2, 8 Hz), 7.12 (1H, s), 7.15 (1H, t, J=54 Hz), 7.2–7.5 (2H, m), 7.5–7.6 (2H, m), 7.9–8.0 (2H, m)

MASS: 381 (M+H)$^+$

(15) 1-(3-Chloro-4-methylphenyl)-3-(difluoromethyl)-5-[4-(methylsulfonyl)phenyl] pyrazole mp: 137–139° C. (ethanol) IR (KBr): 1602, 1313, 1151 cm$^{-1}$ NMR (DMSO-d$_6$, δ): 2.36 (3H, s), 3.25 (3H, s), 7.1–7.2 (1H, m), 7.12 (1H, s), 7.15 (1H, t, J=54 Hz), 7.42 (1H, d, J=8 Hz), 7.53 (1H, d, J=2 Hz), 7.5–7.6 (2H, m), 7.9–8.0 (2H, m)

MASS: 397 (M+H)$^+$

(16) 1-(3-Bromo-4-methylphenyl)-3-(difluoromethyl)-5-[4-(methylsulfonyl)phenyl]pyrazole mp: 136–138° C. (ethanol) IR (KBr): 1602, 1309, 1147 cm$^{-1}$ NMR (DMSO-d$_6$, δ): 2.37 (3H, s), 3.25 (3H, s), 7.12 (1H, s), 7.15 (1H, t, J=54 Hz), 7.18 (1H, dd, J=2, 8 Hz), 7.41 (1H, d, J=8 Hz), 7.5–7.6 (2H, m), 7.68 (1H, d, J=2 Hz), 7.9–8.0 (2H, m)

MASS: 441 (M+H)$^+$

(17) 3-(Difluoromethyl)-1-(3-fluoro-4-methoxyphenyl)-5-[4-(methylsulfonyl)phenyl]pyrazole mp: 185–186° C. (ethanol) IR (KBr): 1596, 1313, 1153 cm$^{-1}$ NMR (DMSO-d$_6$, δ): 3.25 (3H, s), 3.87 (3H, s), 7.11 (1H, s), 7.13 (1H, t, J=54 Hz), 7.1–7.3 (2H, m), 7.3–7.5 (1H, m), 7.5–7.6 (2H, m), 7.9–8.0 (2H, m)

MASS: 397 (M+H)$^+$

(18) 1-(4-Isopropylphenyl)-5-[4-(methylsulfonyl)phenyl]-3-(trifluoromethyl)pyrazole crystals mp: 144–146° C. IR (KBr): 1602, 1506, 1469 cm$^{-1}$ NMR (DMSO-d$_6$, δ): 1.21 (6H, d, J=7 Hz), 2.96 (1H, m ), 3.26 (3H, s), 7.35 (1H, s), 7.30–7.38 (4H, m), 7.56 (2H, d, J=9 Hz), 7.93 (2H, d, J=9 Hz)

MASS: 409 (M+H)$^+$

EXAMPLE 4

To a solution of 1-(3-amino-4-methoxyphenyl)-5-[4-(methylsulfonyl)phenyl]-3-(trifluoromethyl)pyrazole hydrochloride (0.80 g) in ca. 24% hydrobromic acid (16 ml) was added a solution of sodium nitrite (0.14 g) in water (1 ml) while the internal temperature of the reaction mixture was maintained below 0° C. The above mixture was added to an ice-cooled solution of copper(I) bromide (0.30 g) in ca. 24% hydrobromic acid (8 ml) and the mixture was stirred at ambient temperature for 1.5 hours. The reaction mixture was extracted with ethyl acetate and the organic layer was washed with brine, dried over anhydrous magnesium sulfate, and concentrated in vacuo. The residue was purified by column chromatography on silica gel (elution with chloroform) to give the product, which was recrystallized from diisopropyl ether (3 ml)-ethyl acetate (3 ml) to give 1-(3-bromo-4-methoxyphenyl)-5-[4-(methylsulfonyl)phenyl]-3-(trifluoromethyl)-pyrazole (0.39 g).

mp: 164–166° C. (1:1 diisopropyl ether-ethyl acetate) IR (KBr): 1600, 1315, 1164, 1157, 1137 cm$^{-1}$ NMR (DMSO-d$_6$, δ): 3.25 (3H, s), 3.89 (3H, s), 7.17 (1H, d, J=8 Hz), 7.3–7.4 (1H, m), 7.35 (1H, s), 7.5–7.7 (2H, m), 7.75 (1H, d, J=2 Hz), 7.9–8.0 (2H, m)

MASS: 475 (M+H)$^+$

EXAMPLE 5

To a solution of 1-(3-chloro-4-methoxyphenyl)-3-(difluoromethyl)-5-[4-(methylthio)phenyl]pyrazole (2.0 g) in dichloromethane (50 ml) was added portionwise m-chloroperbenzoic acid (2.3 g, 80% purity) at 5° C. with stirring. After being stirred at room temperature for 2 hours, the reaction mixture was treated with aqueous solution of sodium thiosulfate and then partitioned between dichloromethane and water. The organic layer was separated, washed with aqueous sodium hydrogen carbonate solution and dried over magnesium sulfate. After evaporation of the solvent, the crude solid was recrystallized from ethanol to give 1-(3-chloro-4-methoxyphenyl)-3-(difluoromethyl)-5-[4-(methylsulfonyl)phenyl]pyrazole (1.8 g).

mp: 169–171° C. IR (Nujol): 1600, 1510, 1440, 1410, 1350, 1310, 1275, 1150 cm$^{-1}$ NMR (DMSO-d$_6$, δ): 3.25 (3H, s), 3.89 (3H, s), 6.87–7.41 (4H, m), 7.56 (1H, s), 7.57 (1H, d, J=8.2 Hz), 7.94 (2H, d, J=8.5 Hz)

MASS: 413 (M+H)$^+$

EXAMPLE 6

A mixture of sodium methoxide (169 mg) and ethyl 1-(4-fluoro-3-methylphenyl)-5-[4-(methylsulfonyl)phenyl]pyrazole-3-carboxylate (420 mg) in formamide (5 ml) was warmed at 110° C. for 30 minutes. The reaction mixture was poured into ice-water (50 ml) and the precipitate was collected by filtration, and washed with water and dried in vacuo. To an ice-cooled solution of POCl$_3$ (0.23 ml) in dimethylformamide (3 ml) was added the residue by small portions under nitrogen atmosphere. After 2 hours, the mixture was poured into water (50 ml) and stirred for 30 minutes. The resulting precipitates were collected by filtration and washed with water and dried in vacuo. The resulting residue was purified by column chromatography on silica gel using chloroform and was recrystallized from ethanol to afford 1-(4-fluoro-3-methylphenyl)-5-[4-(methylsulfonyl)phenyl]pyrazole-3-carbonitrile (297 mg).

mp: 143.5–144.50° C. IR (KBr): 3118, 2242, 1311, 1232, 1189, 1155 cm$^{-1}$ NMR (CDCl$_3$, δ): 2.29 (3H, d, J=2.0 Hz), 3.08 (3H, s) 6.91–7.26 (4H, m), 7.13 (1H, s), 7.39 (2H, d, J=8.5 Hz), 7.93 (2H, d, J=8.5 Hz)

MASS: 356 (M+H)$^+$ Elemental Analysis for C$_{18}$H$_{14}$FN$_3$O$_2$S Calcd. C, 60.83; H, 3.97; N, 11.82. Found C, 60.57; H, 3.96; N, 11.73.

EXAMPLE 7

The following compounds described in (1) to (10) were obtained according to a similar manner to that of Example 6.

(1) 1-(4-Chloro-3-methylphenyl)-5-[4-(methylsulfonyl)-phenyl]pyrazole-3-carbonitrile mp: 163.0–164.0° C. IR (KBr): 3118, 3010, 1710, 2240, 1313, 1155 cm$^{-1}$ NMR (CDCl$_3$, δ): 2.39 (3H, s), 3.09 (3H, s), 6.92 (1H, dd, J=8.4, 2.5 Hz), 6.96 (1H, s), 7.30 (1H, d, J=2.5 Hz), 7.34 (1H, d, J=8.4 Hz), 7.42 (2H, d, J=8.5 Hz), 7.95 (2H, d, J=8.5 Hz)

MASS: 372 (M+H)$^+$ ($^{35}$Cl), 374 (M+H)$^+$ ($^{37}$Cl)

(2) 1-(4-Bromo-3-methylphenyl)-5-[4-(methylsulfonyl)phenyl]pyrazole-3-carbonitrile mp: 151.5–152.5° C. IR (KBr): 3120, 3010, 2242, 1313, 1153 cm$^{-1}$ NMR (CDCl$_3$, δ): 2.41 (3H, s), 3.09 (3H, s), 6.83 (1H, dd, J=8.4, 2.3 Hz), 6.96 (1H, s), 7.30 (1H, d, J=2.3 Hz), 7.42 (2H, d, J=8.6 Hz), 7.53 (1H, d, J=8.4 Hz), 7.95 (2H, d, J=8.6 Hz)

MASS: 416 (M+H)$^+$ ($^{79}$Br), 418 (M+H)$^+$ ($^{81}$Br)

(3) 1-(4-Fluoro-3-methoxyphenyl)-5-[4-(methylsulfonyl)-phenyl]pyrazole-3-carbonitrile mp: 169.0–171.0° C. IR (KBr): 3126, 3085, 2242, 1309, 1268, 1249, 1149 cm$^{-1}$ NMR (CDCl$_3$, δ): 3.08 (3H, d, J=1.9 Hz), 3.85 (3H, s), 6.65 (1H, m), 6.97–7.06 (3H, m), 7.43 (2H, d, J=8.5 Hz), 7.92 (2H, d, J=8.5 Hz)

MASS: 372 (M+H)$^+$ (4) 1-(4-Chloro-3-methoxyphenyl)-5-[4-(methylsulfonyl)-phenyl]pyrazole-3-carbonitrile mp: 203.0–205.0° C. IR (KBr): 3120, 2252, 1309, 1238, 1147 cm$^{-1}$ NMR (CDCl$_3$, δ): 3.09 (3H, s), 3.85 (3H, s), 6.64

(1H, dd, J=8.4, 2.4 Hz), 6.97 (1H, s), 7.00 (1H, d, J=2.4 Hz), 7.33 (1H, d, J=8.4 Hz), 7.44 (2H, d, J=8.5 Hz), 7.96 (2H, d, J=8.5 Hz)

MASS: 388 (M+H)$^+$ ($^{35}$Cl), 390 (M+H)$^{35}$ ($^{37}$Cl)

(5) 1-($^4$-Bromo-3-methoxyphenyl)-5-[4-(methylsulfonyl)-phenyl]pyrazole-3-carbonitrile mp: 212.5–214.5° C. IR (KBr): 3118, 2252, 1307, 1236, 1149 cm$^{-1}$ NMR (CDCl$_3$, δ): 3.09 (3H, s), 3.85 (3H, s), 6.56 (1H, dd, J=8.4, 2.3 Hz), 6.96 (1H, d, J=2.3 Hz), 7.44 (2H, d, J=8.3 Hz), 7.51 (1H, d, J=8.4 Hz), 7.96 (2H, d, J=8.3 Hz)

MASS: 432 (M+H)$^+$ ($^{79}$Br), 434 (M+H)$^+$ ($^{81}$Br)

(6) 1-(3-Fluoro-4-methylphenyl)-5-[4-(methylsulfonyl)-phenyl]pyrazole-3-carbonitrile mp: 167.0–168.0° C. IR (KBr): 3129, 3072, 2250, 1363, 1149 cm$^{-1}$ NMR (CDCl$_3$, δ): 2.32 (3H, d, J=1.9 Hz), 3.09 (3H, s), 6.90 (1H, dd, J=8.1, 2.1 Hz), 6.95 (1H, s), 7.03 (1H, dd, J=9.5, 2.1 Hz), 7.19 (1H, t, J=8.1 Hz), 7.42 (2H, d, J=8.6 Hz), 7.95 (2H, d, J=8.6 Hz)

MASS: 356 (M+H)$^+$ Elemental Analysis for C$_{18}$H$_{14}$FN$_3$O$_2$S.1/2H$_2$O Calcd. C, 59.33; H, 4.15; N, 11.53. Found C, 59.53; H, 3.88; N, 11.50.

(7) 1-(3-Chloro-4-methylphenyl)-5-[4-(methylsulfonyl)-phenyl]pyrazole-3-carbonitrile mp: 174.5–175.50° C. IR (KBr): 3120, 3012, 2244, 1317, 1151 cm$^{-1}$ NMR (CDCl$_3$, δ): 2.42 (3H, s), 3.08 (3H, s), 6.95–7.00 (2H, m), 7.24 (1H, d, J=8.4 Hz), 7.40 (1H, s), 7.42 (2H, d, J=8.3 Hz), 7.95 (2H, d, J=8.3 Hz)

MASS: 372 (M+H)$^+$ ($^{35}$Cl), 374 (M+H)$^+$ ($^{37}$Cl) Elemental Analysis for C$_{18}$H$_{14}$ClN$_3$O$_2$S Calcd. C, 58.14; H, 3.79; N, 11.30. Found C, 57.88; H, 3.74; N, 11.14.

(8) 1-(3-Bromo-4-methylphenyl)-5-[4-(methylsulfonyl)phenyl]pyrazole-3-carbonitrile mp: 179.0–180.0° C. IR (KBr): 3120, 3010, 2246, 1317, 1151 cm$^{-1}$ NMR (CDCl$_3$, δ): 2.44 (3H, s), 3.08 (3H, s), 6.96 (1H, s), 7.01 (1H, dd, J=8.1, 2.1 Hz), 7.24 (1H, d, J=8.1 Hz), 7.42 (2H, d, J=8.6 Hz), 7.58 (1H, d, J=2.1 Hz), 7.95 (2H, d, J=8.6 Hz)

MASS: 416 (M+H)$^+$ ($^{79}$Br), 418 (M+H)$^+$ ($^{81}$Br)

(9) 1-(3-Fluoro-4-methoxyphenyl)-5-[4-(methylsulfonyl)-phenyl]pyrazole-3-carbonitrile mp: 192.0–193.0° C. IR (KBr): 3068, 3016, 2252, 1315, 1278, 1151 cm$^{-1}$ NMR (CDCl$_3$, δ) 3.09 (3H, s), 3.94 (3H, s), 6.94–6.96 (3H, m), 7.12 (1H, dd, J=10.1, 2.1 Hz), 7.42 (2H, d, J=8.5 Hz), 7.94 (2H, d, J=8.5 Hz)

MASS: 372 (M+H)$^+$

(10) 1-(3-Chloro-4-methoxyphenyl)-5-[4-(methylsulfonyl)-phenyl]pyrazole-3-carbonitrile mp: 201.0–203° C. IR (KBr): 3016, 2250, 1311, 1274, 1151 cm$^{-1}$ NMR (CDCl$_3$, δ): 3.08 (3H, s), 3.95 (3H, s), 6.89 (1H, d, J=8.8 Hz), 6.95 (1H, s), 7.05 (1H, dd, J=8.8, 2.6 Hz), 7.42 (2H, d, J=8.6 Hz), 7.43 (1H, d, J=2.6 Hz), 7.95 (2H, d, J=8.6 Hz)

MASS: 388 (M+H)$^+$ ($^{35}$Cl), 390 (M+H)$^+$ ($^{37}$Cl)

EXAMPLE 8

The following compound was obtained according to a similar manner to that of Example 4.

1-(3-Bromo-4-methoxyphenyl)-5-[4-(methylsulfonyl)-phenyl]pyrazole-3-carbonitrile mp: 184.0–186.0° C. IR (KBr): 3064, 3016, 2240, 1309, 1274, 1151 cm$^{-1}$ NMR (CDCl$_3$, δ): 3.08 (3H, s), 3.94 (3H, s), 6.86 (1H, d, J=8.8 Hz), 6.95 (1H, s), 7.09 (1H, dd, J=8.8, 2.6 Hz), 7.42 (2H, d, J=8.4 Hz), 7.60 (1H, d, J=2.6 Hz), 7.95 (2H, d, J=8.4 Hz)

MASS: 432 (M+H)$^+$ ($^{79}$Br), 434 (M+H)$^+$ ($^{81}$Br) Elemental Analysis for C$_{18}$H$_{14}$BrN$_3$O$_3$S Calcd. C, 50.01; H, 3.26; N, 9.72. Found C, 49.75; H, 3.15; N, 9.59.

EXAMPLE 9

To a solution of {1-(3-methoxyphenyl)-5-[4-(methylthio) phenyl]pyrazole-3-yl}amine (5 g) in acetic acid (40 ml) and hydrochloric acid (10 ml) was added sodium nitrite (1.7 g) in water (3 ml) at 0° C. This mixture was stirred at 0° C. for 1 hour. The diazonium salt prepared above was added to a solution of copper(I) chloride (7 g) in hydrochloric acid (10 ml) at 0° C., and then allowed to warm to ambient temperature. After 1 hour, the reaction mixture was poured into ice water, and extracted with dichloromethane. The organic layer was dried over magnesium sulfate, and filtered. The filtrate was evaporated in vacuo and purified by column chromatography on silica gel eluting with a mixed solution of dichloromethane and n-hexane (1:1). The desired product was dissolved in methanol (100 ml). A solution of Oxone® (potassium peroxy monosulfate) (20 g) in water was added at room temperature and the resultant mixture was stirred for 1 hour and then filtered. The filtrate was extracted with dichloromethane, and washed with water twice. The organic layer was dried over magnesium sulfate, and filtered. The filtrate was evaporated in vacuo to give 3-chloro-1-(3-methoxyphenyl)-5-[4-(methylsulfonyl)phenyl]pyrazole (1.32 g).

mp: 103–104° C. IR (Nujol): 1600 cm$^{-1}$ NMR (DMSO-d$_6$, δ): 3.24 (3H, s), 3.71 (3H, s), 6.71–6.82 (1H, m), 6.93–7.03 (3H, m), 7.29–7.37 (1H, m) 7.53 (2H, d, J=8.5 Hz), 7.92 (2H, d, J=8.5 Hz)

MASS: 363 (M+H)$^+$

EXAMPLE 10

The following compounds described in (1) to (14) were obtained according to a similar manner to that of Example 9.

(1) 3-Chloro1-(4-fluoro-3-methylphenyl)-5-[4-(methylsulfonyl)phenyl]pyrazole IR (KBr): 1598, 1502 cm$^{-1}$ NMR (CDCl$_3$, δ): 2.26 and 2.27 (total 3H, each s), 3.07 (3H, s), 6.52 (1H, s), 6.92 (1H, t, J=3.3 Hz), 6.96 (1H, t, J=8.6 Hz), 7.21–7.26 (1H, m), 7.40 (2H, dt, J=8.5, 1.9 Hz), 7.90 (2H, dt, J=8.5, 1.8 Hz).

MASS: 365 (M$^+$)

(2) 3-Chloro-1-(4-chloro-3-methylphenyl)-5-[4-(methylsulfonyl)phenyl]pyrazole mp: 180–181° C. IR (Nujol): 1625, 1590 cm$^{-1}$ NMR (DMSO-d$_6$, δ): 2.33 (3H, s), 3.25 (3H, s), 6.98 (1H, s), 7.05 (1H, dd, J=8.4, 2.5 Hz), 7.44–7.49 (2H, m), 7.53 (2H, d, J=8.5 Hz), 7.93 (2H, d, J=8.5 Hz)

MASS: 382 (M+H)$^+$

(3) 1-(4-Bromo-3-methylphenyl)-3-chloro-5-[4-(methylsulfonyl)phenyl]pyrazole mp: 146–1413° C. IR (Nujol): 1600 cm$^{-1}$ NMR (DMSO-d$_6$, δ): 2.35 (3H, s), 3.25 (3H, s), 6.93–6.99 (1H, m), 6.99

(1H, s), 7.48 (1H, d, J=2.4 Hz), 7.54 (2H, d, J=8.4 Hz), 7.61 (1H, d, J=8.5 Hz), 7.94 (1H, d, J=8.4 Hz)

MASS: 426 (M+H)$^+$ (4) 3-Chloro-1-(4-chloro-3-methoxyphenyl)-5-[4-(methylsulfonyl)phenyl]pyrazole mp: 165–1660° C. IR (Nujol): 1590 cm$^{-1}$ NMR (DMSO-d$_6$, δ): 3.25 (3H, s), 3.76 (3H, s), 6.81 (1H, dd, J=8.4, 2.3 Hz), 7.00 (1H, s), 7.18 (1H, d, J=2.3 Hz), 7.47 (1H, d, J=8.4 Hz), 7.56 (2H, d, J=8.5 Hz), 7.95 (1H, d, J=8.5 Hz)

MASS: 398 (M+H)$^+$ (5) 3-Chloro-1-(3-fluoro-4-methylphenyl)-5-[4-(methyl-sulfonyl)phenyl]pyrazole mp: 160–162° C. IR (KBr): 1614, 1590, 1509 cm$^{-1}$ NMR (DMSO-d$_6$, δ): 2.25 and 2.26 (total 3H, each s), 3.25 (3H, s), 6.97 (1H, s), 7.00 (1H, dd, J=8.8, 1.9 Hz), 7.25 (1H, dd, J=10.3, 2.0 Hz), 7.34 (1H, t, J=8.3 Hz), 7.53 (2H, d, J=8.4 Hz), 7.93 (2H, d, J=8.4 Hz)

MASS: 365 (M+H)$^+$ (6) 3-Chloro-1-(3-chloro-4-methylphenyl)-5-[4-(methylsulfonyl)phenyl]pyrazole mp: 159–161° C. IR (Nujol): 1610 cm$^{-1}$ NMR (DMSO-d$_6$, δ) 2.35 (3H, s), 3.25 (3H, s), 6.98 (1H, s), 7.11 (1H, dd, J=8.2, 2.2 Hz), 7.39 (1H, d, J=8.3 Hz), 7.51 (1H, d, J=2.2 Hz), 7.54 (2H, d, J=8.4 Hz), 7.94 (2H, d, J=8.4 Hz)

MASS: 382 (M+H)$^+$ (7) 1-(3-Bromo-4-methylphenyl)-3-chloro-5-[4-(methylsulfonyl)phenyl]pyrazole IR (Nujol): 1600 cm$^{-1}$ NMR (DMSO-d$_6$, δ): 2.37 (3H, s), 3.25 (3H, s), 7.14 (1H, dd, J=8.1, 2.2 Hz), 6.69 (1H, s), 7.39 (1H, d, J=8.3 Hz), 7.54 (2H, d, J=8.5 Hz), 7.65 (1H, d, J=2.2 Hz), 7.94 (2H, d, J=8.5 Hz)

MASS: 426 (M+H)$^+$ (8) 3-Chloro-1-(3-chloro-4-methoxyphenyl)-5-[4-(methylsulfonyl)phenyl]pyrazole mp: 179–180° C. IR (Nujol): 1600 cm$^{-1}$ NMR (DMSO-d$_6$, δ): 3.25 (3H, s), 3.89 (3H, s), 6.97 (1H, s), 7.17 (1H, d, J=8.8 Hz), 7.23 (1H, d, J=8.8 Hz), 7.53 (2H, d J=8.6 Hz), 7.55 (1H, s), 7.93 (2H, d, J=8.5 Hz)

MASS: 398 (M+H)$^+$ (9) 3-Chloro-1-(4-ethylphenyl)-5-[4-(methylsulfonyl)phenyl]pyrazole crystals mp: 167–169° C. IR (Nujol): 1510 cm$^{-1}$ NMR (DMSO-d$_6$, δ): 1.19 (3H, t, J=8 Hz), 2.65 (2H, q, J=8 Hz), 3.25 (3H, s), 6.95 (1H, s), 7.22 (2H, d, J=9 Hz), 7.29 (2H, d, J=9 Hz), 7.50 (2H, d, J=9 Hz), 7.92 (2H, d, J=9 Hz)

MASS: 361 (M+H)$^+$

(10) 3-Chloro-1-(3-chloro-4-ethylphenyl)-5-[4-(methylsulfonyl)-phenyl]pyrazole crystals mp: 125–120° C. IR (KBr): 1598, 1490 cm$^{-1}$ NMR (DMSO-d$_6$, δ): 1.18 (3H, t, J=7 Hz), 2.72 (2H, q, J=7 Hz), 3.25 (3H, s), 6.98 (1H, d, J=2 Hz), 7.13 (1H, dd, J=8, 2 Hz), 7.39 (1H, dd, J=8, 2 Hz), 7.50 (1H, d, J=2 Hz), 7.55 (2H, d, J=8 Hz), 7.91 (2H, d, J=8 Hz)

MASS: 395 (M+H)$^+$ ($^{35}$Cl), 397 (M+H)$^+$ ($^{37}$Cl)

(11) 3-Chloro-5-[4-(methylsulfonyl)phenyl]-1-(4-n-propylphenyl)-pyrazole crystals mp: 143–144° C. IR (KBr): 1513 cm$^{-1}$ NMR (DMSO-d$_6$, δ): 0.89 (3H, t, J=7 Hz), 1.54–1.65 (2H, m), 2.59 (2H, t, J=7 Hz), 3.25 (3H, s), 6.96 (1H, s), 7.19–7.30 (4H, m), 7.50 (2H, d, J=9 Hz), 7.90 (2H, d, J=9 Hz)

MASS: 375 (M+H)$^+$

(12) 3-Chloro-1-(3-chloro-4-n-propylphenyl)-5-[4-(methylsulfonyl)-phenyl]pyrazole crystals mp: 119–122° C. IR (KBr): 1602, 1490 cm$^{-1}$ NMR (DMSO-d$_6$, δ): 0.92 (3H, t, J=7 Hz), 1.57 (2H, dt, J=7 Hz), 2.69 (2H, t, J=7 Hz), 3.25 (3H, s), 6.99 (1H, s), 7.13 (1H, dd, J=8, 2 Hz), 7.38 (1H, d, J=8 Hz), 7.51 (1H, d, J=2 Hz), 7.54 (2H, d, J=8 Hz), 7.94 (2H, d, J=8 Hz)

MASS: 409 (M+H)$^+$

(13) 1-(3-Chloro-4-isopropylphenyl)-5-[4-(methylsulfonyl)phenyl]-3-(trifloromethyl)pyrazole crystals mp: 84–86° C. IR (KBr) 1602, 1490, 1469 cm$^{-1}$ NMR (DMSO-d$_6$, δ): 1.21 (6H, d, J=7 Hz), 3.30 (1H, m), 3.27 (3H, s), 7.27–7.63 (6H, m), 7.69 (2H, d, J=9 Hz)

MASS: 443 (M+H)$^+$

(14) 3-Chloro-1-(4-isopropylphenyl)-5-[4-(methylsulfonyl)phenyl]pyrazole crystals mp: 146–148° C. IR (KBr): 1513 cm$^{-1}$ NMR (DMSO-d$_6$, δ): 1.21 (6H, d, J=7 Hz), 2.90–2.97 (1H, m), 3.25 (3H, s), 6.96 (1H, s), 7.10–7.40 (4H, m), 7.51 (2H, d, J=9 Hz), 7.9 (2H, d, J=9 Hz)

MASS: 375 (M+H)$^+$

EXAMPLE 11

A solution of sodium nitrite (0.1 g) in water (0.2 ml) was added a solution of 1-(4-amino-3-methoxyphenyl)-3-chloro-5-[4-(methylsulfonyl)phenyl]pyrazle (0.38 g) in concentrated hydrochloric acid (2 ml) at 0° C. with stirring. The reaction mixture was stirred at 0° C. for 1 hour. 42% Tetrafluoroboric acid (0.5 ml) was added to the solution containing the diazonium salt at 0° C. The resulting mixture was stirred at 0° C. for 2 hours and then left in a refrigerator overnight. The resulting precipitate was collected by filtration, washed with ice water and dried in vacuo, which was heated at 180–200° C. for 10 minutes. Ice water was added and the resulting mixture was extracted with a mixture of tetrahydrofuran and ethyl acetate (1:1). The extract was washed with brine, dried over magnesium sulfate and evaporated under reduced pressure. The residue was subjected to column chromatography on silica gel using a mixture of isopropyl ether and tetrahydrofuran (5:1) as eluent to give 3-chloro-1-(4-fluoro-3-methoxyphenyl)-5-[4-(methylsulfonyl)phenyl]pyrazole (55mg).

mp: 140–145° C. (decomp.) IR (Nujol): 1600, 1510, 1310, 1250, 1150 cm$^{-1}$ NMR (DMSO-d$_6$, δ): 3.89 (3H, s), 4.01 (3H, s), 6.56 (1H, s), 6.95 (1H, d, J=6.0 Hz), 7.21–7.32 (2H, m), 7.53 (2H, d, J=8.0 Hz), 7.92 (2H, d, J=8.0 Hz)

MASS: 365 (M+H)$^+$

EXAMPLE 12

A solution of m-chloroperbenzoic acid (0.40 g) in dichloromethane (4 ml) was added dropwise to a solution of 3-chloro-1-(3-cyano-4-methoxyphenyl)-5-[4-(methylthio)phenyl]pyrazole (0.23 g) in dichloromethane (5 ml) and stirred at 0° C. for 1 hour. The mixture was washed with an aqueous solution of sodium bicarbonate, dried over magnesium sulfate, and concentrated under reduced pressure. The residue was purified by column chromatography on silica gel eluting with a mixture of toluene and ethyl acetate (5:1) to give crystals of 3-chloro-1-(3-cyano-4-methoxyphenyl)-5-[4-(methylsulfonyl)-phenyl]pyrazole (197 mg).

mp: 191–194° C. IR (Nujol) 2235, 1604, 1310, 1150 cm$^{-1}$ NMR (CDCl$_3$, δ): 3.10 (3H, s), 3.98 (3H, s), 6.54 (1H, s), 6.95 (1H, d, J=9.0 Hz), 7.38 (1H, dd, J=9.0, 2.6 Hz), 7.40 (2H, d, J=8.6 Hz), 7.54 (1H, d, J=2.6 Hz), 7.94 (2H, d, J=8.6 Hz)

MASS: 388 (M+H)$^+$

EXAMPLE 13

To a stirred solution of 3-chloro-1-(4-methoxyphenyl)-5-[4-(methylsulfonyl)phenyl]pyrazole (278 mg) in a mixture of acetic anhydride (5 ml) and acetic acid (5 ml), nitric acid (sp. gr. 1.42) (0.5 ml) was added at 0° C. After 30 minutes, the resulting mixture was poured into water and extracted with ethyl acetate. The extract was washed with brine, dried over magnesium sulfate, and concentrated under reduced pressure to give crystals. The resulting crystals were washed with ethyl acetate to give 3-chloro-1-(4-methoxy-3-nitrophenyl)-5-[4-(methylsulfonyl)phenyl]pyrazole (297 mg).

mp: 178–180° C. (decomp.) IR (Nujol): 1620, 1600, 1535 cm$^{-1}$ NMR (CDCl$_3$, δ): 3.09 (3H, s), 4.00 (3H, s), 6.55 (1H, s), 7.07 (1H, d, J=9.0 Hz), 7.40 (1H, dd, J=9.0, 2.7 Hz), 7.44 (2H, d, J=8.5 Hz), 7.75 (1H, d, J=2.7 Hz), 7.95 (2H, d, J=8.5 Hz)

MASS: 408 (M+H)$^+$

Industrial Applicability

The compound (I) and a salt thereof of the present invention have selective inhibitory activity of COX-II and are useful for the treatment and/or prevention of inflammatory conditions, various pains, collagen diseases, autoimmune diseases, various immunity diseases, thrombosis, cancer or neurodegenerative diseases and the like.

This application is based on application No. PO9414 filed in Australia, the content of which is incorporated hereinto by reference.

What is claimed is:

1. A compound of the formula (I):

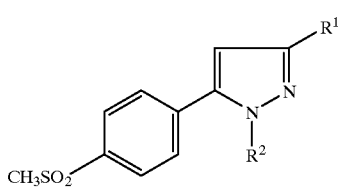

(I)

wherein R$^1$ is chlorine, difluoromethyl, trifluoromethyl or cyano; and
R$^2$ is a group having the formula:

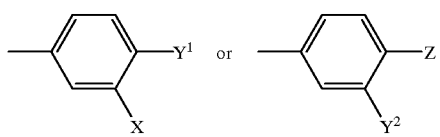

wherein
X is halogen, cyano, nitro or amino;
Y$^1$ is lower alkyl or lower alkoxy;
Y$^2$ is lower alkyl or lower alkoxy; and Z is halogen;

or a pharmaceutically acceptable salt thereof.

2. The compound of claim 1, wherein

R$^1$ is chlorine; and

R$^2$ is a group having the formula:

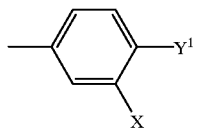

wherein X is halogen or cyano; and Y$^1$ is lower alkoxy.

3. The compound of claim 1, which is a compound selected from the group consisting of 3-chloro-1-(3-cyano-4-methoxyphenyl)-5-[4-(methylsulfonyl)phenyl]pyrazole, 3-chloro-1-(3-chloro-4-methoxyphenyl)-5-[4-(methylsulfonyl)phenyl]pyrazole, 3-chloro-1-(3-chloro-4-methylphenyl)-5-[4-(methylsulfonyl)-phenyl]pyrazole, 3-chloro-1-(3-fluoro-4-methylphenyl)-5-[4-(methylsulfonyl)-phenyl]pyrazole, 1-(3-fluoro-4-methoxyphenyl)-5-[4-(methylsulfonyl)phenyl]-3-(trifluoromethyl)pyrazole, 3-(difluoromethyl)-1-(3-fluoro-4-methoxyphenyl)-5-[4-(methylsulfonyl)phenyl]pyrazole, 3-chloro-1-(4-chloro-3-methylphenyl)-5-[4-(methylsulfonyl)phenyl]pyrazole, and 1-(4-chloro-3-methoxyphenyl)-5-[4-(methylsulfonyl)-phenyl]pyrazole-3-carbonitrile.

4. The compound of claim 1, which is 3-chloro-1-(3-chloro-4-ethylphenyl)-5-[4-(methylsulfonyl)-phenyl]pyrazole.

5. A pharmaceutical composition, comprising one or more compounds of claim 1, as an active ingredient, in association with a pharmaceutically acceptable carrier or excipient.

6. A method of treating a disease or condition in a mammal by inhibiting activity of cyclooxygenase-2 (COX II), which comprises administering an effective amount of one or more of the compounds of claim 1, to a mammal in need thereof.

7. The method of claim 6, wherein said mammal is a human.

8. The method of claim 6, which comprises treating inflammation.

9. The method of claim 6, which comprises effecting analgesia.

10. The method of claim 6, which comprises treating thrombosis.

11. The method of claim 6, which comprises treating rheumatoid arthritis.

12. The method of claim 6, which comprises treating Alzheimer's disease.

13. A compound of the formula (I)

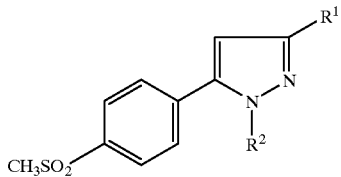

wherein:
R¹ is chlorine, difluoromethyl, trifluoromethyl or cyano; and
R² is a group having the formula:

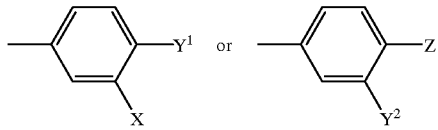

wherein:
X is halogen, cyano, or nitro;
Y¹ is lower alkyl or lower alkoxy;
Y² is lower alkyl or lower alkoxy; and
Z is halogen.

14. The compound of claim 1, wherein:
R¹ is trifluoromethyl; and
R² is a group having the formula:

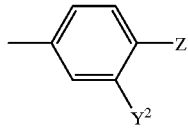

wherein Y² is lower alkyl; and Z is halogen.

* * * * *